(12) United States Patent
Galliher et al.

(10) Patent No.: US 7,819,934 B2
(45) Date of Patent: Oct. 26, 2010

(54) ENVIRONMENTAL CONTAINMENT SYSTEMS

(75) Inventors: Parrish M. Galliher, Littleton, MA (US); Geoffrey L. Hodge, Sutton, MA (US); Michael Fisher, Ashland, MA (US)

(73) Assignee: Xcellerex, Inc., Marlborough, MA (US)

( * ) Notice: Subject to any disclaimer, the term of this patent is extended or adjusted under 35 U.S.C. 154(b) by 544 days.

(21) Appl. No.: 11/879,033

(22) Filed: Jul. 13, 2007

(65) Prior Publication Data
US 2008/0139865 A1 Jun. 12, 2008

Related U.S. Application Data

(60) Provisional application No. 60/830,997, filed on Jul. 14, 2006.

(51) Int. Cl.
*B01D 50/00* (2006.01)
(52) U.S. Cl. .................. 55/385.2; 55/418; 55/DIG. 18; 454/187; 454/192; 312/1
(58) Field of Classification Search ............... 55/385.1, 55/385.2, 418, 471, DIG. 18, DIG. 46; 454/187, 454/192; 128/205.11, 205.26; 600/21; 135/116, 135/119, 127; 312/1
See application file for complete search history.

(56) References Cited

U.S. PATENT DOCUMENTS

| | | | |
|---|---|---|---|
| 3,397,631 A * | 8/1968 | Simons | 454/190 |
| 4,620,794 A | 11/1986 | Leka | |
| 4,671,667 A | 6/1987 | Augustin | |
| 4,696,902 A | 9/1987 | Bisconte | 435/300 |
| 5,205,783 A | 4/1993 | Dieckert et al. | |
| 5,219,215 A | 6/1993 | Akagawa | 312/1 |
| 5,326,316 A | 7/1994 | Hashimoto et al. | |
| 5,385,546 A | 1/1995 | Kriesel et al. | |

(Continued)

FOREIGN PATENT DOCUMENTS

CA 2271583 C 4/2002

(Continued)

OTHER PUBLICATIONS

International Search Report and Written Opinion dated Jul. 8, 2008, for PCT/US2007/015954 (the parent case), 13 pages (in English).

(Continued)

*Primary Examiner*—Duane Smith
*Assistant Examiner*—Minh-Chau Pham
(74) *Attorney, Agent, or Firm*—Jacqueline Arendt

(57) ABSTRACT

Environmental containment systems, and in certain embodiments, systems and methods involving vessels and unit operations or components of cell culture, cell containment, bioreactor, chemical manufacturing, or pharmaceutical manufacturing systems provided with environmental containment are provided. Certain vessels, unit operations, devices, and components may be used to perform all or part of biological, chemical, and/or pharmaceutical manufacturing processes therein. In some embodiments, an environmental containment system includes a multi-level containment apparatus. For instance, a first substantially closed environmental containment enclosure may be contained within a second substantially closed environmental containment enclosure; the first and second enclosures may be contained in a third substantially closed environmental containment enclosure, etc. Each of the environments within the substantially closed environmental containment enclosures may be controlled independently, and leakage of any materials from an inner system may be contained by an outer system.

17 Claims, 12 Drawing Sheets

U.S. PATENT DOCUMENTS

| | | | |
|---|---|---|---|
| 5,401,212 | A | 3/1995 | Marvell et al. |
| 5,407,564 | A | 4/1995 | Thrailkill |
| 5,487,768 | A | 1/1996 | Zytka et al. |
| 5,577,837 | A | 11/1996 | Martin et al. ............... 366/145 |
| 5,591,344 | A | 1/1997 | Kenley et al. |
| 5,656,491 | A | 8/1997 | Cassani et al. |
| 5,728,581 | A | 3/1998 | Schwartz et al. |
| 5,730,777 | A * | 3/1998 | Petersen et al. ............... 95/12 |
| 5,783,072 | A | 7/1998 | Kenley et al. |
| 5,843,196 | A * | 12/1998 | Leavey et al. ............... 55/356 |
| 6,349,237 | B1 | 2/2002 | Koren et al. |
| 6,353,786 | B1 | 3/2002 | Yamada et al. |
| 6,379,428 | B1 | 4/2002 | Mostovoy et al. |
| 6,425,414 | B2 | 7/2002 | Jorgensen et al. |
| 6,432,698 | B1 | 8/2002 | Gaugler et al. |
| 6,473,668 | B2 | 10/2002 | Abuzeid et al. |
| 6,514,137 | B1 | 2/2003 | Panelli et al. |
| 6,544,788 | B2 | 4/2003 | Singh |
| 6,555,011 | B1 | 4/2003 | Tribelsky et al. |
| 6,670,171 | B2 | 12/2003 | Carll |
| 6,912,443 | B2 | 6/2005 | Duemler |
| 7,156,897 | B2 * | 1/2007 | Wen ............................. 95/28 |
| 7,204,751 | B2 * | 4/2007 | Jang et al. .................. 454/187 |
| 7,285,147 | B2 * | 10/2007 | Kuo et al. ................. 55/385.2 |
| 7,335,243 | B2 * | 2/2008 | Homan et al. ............. 55/385.2 |
| 2003/0170810 | A1 | 9/2003 | Vedadi et al. |
| 2004/0229335 | A1 | 11/2004 | Zhang et al. |
| 2005/0226794 | A1 * | 10/2005 | Hodge et al. ............... 422/243 |
| 2005/0272146 | A1 * | 12/2005 | Hodge et al. ............. 435/289.1 |
| 2006/0003685 | A1 | 1/2006 | Rothbauer et al. |
| 2007/0039294 | A1 * | 2/2007 | Airey ....................... 55/385.2 |

FOREIGN PATENT DOCUMENTS

| | | |
|---|---|---|
| DE | 19917398 A1 | 10/2000 |
| EP | 0 990 699 A1 | 4/2000 |
| GB | 1 396 883 | 6/1975 |
| JP | 07 158919 | 6/1995 |

OTHER PUBLICATIONS

International Preliminary Report on Patentability dated Jan. 14, 2009, for PCT/US2007/015954 (the parent case), 2 pages (in English).

* cited by examiner

ENVIRONMENTAL CONTAINMENT SYSTEMS

RELATED APPLICATIONS

This application claims priority under 35 U.S.C. 119(e) to U.S. Provisional Patent Application No. 60/830,997, filed Jul. 14, 2006, and entitled "Stirred Tank Bioreactor having Environmental Containment", which is incorporated herein by reference.

FIELD OF INVENTION

The present invention relates generally to environmental containment systems, and in certain embodiments, to systems and methods involving vessels and unit operations or components of cell culture, cell containment, bioreactor, chemical manufacturing, or pharmaceutical manufacturing systems provided with environmental containment.

BACKGROUND

A variety of vessels, devices, components and unit operations for manipulating fluids and/or for carrying out chemical, biochemical and/or biological processes are available. For instance, biological materials (e.g., animal and plant cells) including, for example, mammalian, plant or insect cells and microbial cultures can be processed using bioreactors. Traditional bioreactors, which are typically designed as stationary reusable tanks or containers, or disposable bioreactors, many of which utilize plastic sterile bags, may be used for such purposes. Although chemical manufacturing systems, pharmaceutical manufacturing systems, bioreactor systems and other fluid manipulating systems (e.g., mixing systems) are known, improvements to such systems would be beneficial. In particular, systems which include environmental containment that can maintain a sterile, aseptic, substantially particle-free, or reduced-particle environment around or in the system would be useful in a variety of fields, especially for applications involving cell culture, clean manufacturing processes, and use of dangerous materials and/or infectious agents.

SUMMARY OF THE INVENTION

The present invention relates generally to environmental containment systems, and in certain embodiments, to systems and methods involving vessels or other devices provided with environmental containment. The vessels or devices may, in certain embodiments, be adapted for containing and manipulating fluids. Certain such vessels may be used to perform biological, chemical, and/or pharmaceutical manufacturing processes therein. The subject matter of the present invention involves, in some cases, interrelated products, alternative solutions to a particular problem, and/or a plurality of different uses of one or more systems and/or articles.

In one aspect of the invention, a series of apparatuses are provided. In one embodiment, an apparatus includes a vessel comprising a container adapted for containing a liquid and an environmental containment enclosure surrounding at least a portion of the vessel, the environmental containment enclosure being configured so that at least a portion of the environmental containment enclosure has a shape and/or contour that is complementary to a shape and/or contour of an outer surface of the vessel to which the at least a portion of the environmental containment enclosure is adjacent. The apparatus may include a gap between an inner surface of the environmental containment enclosure and the outer surface of the vessel defining an enclosed space. At least a portion of the gap may be positioned between the vessel and the inner surface of the environmental containment enclosure. In some cases, the enclosed space is not in continuous fluid communication with an interior portion of the container. The apparatus may optionally include an environmental treatment system in communication with the enclosed space, wherein the environmental treatment system and environmental containment enclosure are configured to maintain an aseptic and/or substantially particle-free environment within the enclosed space.

In another embodiment, an apparatus comprises at least one device configured for containing a fluid or biological cells comprising at least a part of a cell culture, cell containment, bioreactor, chemical manufacturing, or pharmaceutical manufacturing system. The apparatus may include a first environmental containment enclosure surrounding at least a portion of the vessel. A first gap may be formed between an inner surface of the environmental containment enclosure and the outer surface of the vessel defining a first enclosed space positioned between the vessel and the inner surface of the environmental containment enclosure. In some cases, the first enclosed space is not in continuous fluid communication with an interior portion of the container. The apparatus may optionally include a second environmental containment enclosure surrounding at least a portion of the first environmental containment enclosure. A second gap may be formed between an inner surface of the second environmental containment enclosure and an outer surface of the first environmental containment enclosure, defining a second enclosed space positioned between the inner surface of the second environmental containment enclosure and the outer surface of the first environmental containment enclosure. In some cases, the second enclosed space is not in continuous fluid communication with an interior portion of the container. The apparatus may optionally include an environmental treatment system in communication with at least one of the first and second enclosed spaces, wherein the environmental treatment system and the environmental containment enclosures are configured to maintain an aseptic and/or substantially particle-free environment within the at least one of the first and second enclosed spaces.

In another embodiment, an apparatus comprises a vessel which may be a container, or part of a container, adapted for containing a liquid or a unit operation component adapted for performing a biological, chemical, and/or pharmaceutical manufacturing process. An environmental containment enclosure may be irreversibly attached to and surround at least a portion of the vessel. A gap may be formed between an inner surface of the environmental containment enclosure and an outer surface of the vessel defining an enclosed space, at least a portion of which is positioned between the vessel and the inner surface of the environmental containment enclosure. In some cases, the enclosed space is not in continuous fluid communication with the container for containing a liquid. The apparatus may optionally include an environmental treatment system in fluid communication with the enclosed space, wherein the environmental treatment system and environmental containment enclosure are configured to maintain an aseptic and/or substantially particle-free environment within the enclosed space.

In another embodiment, an apparatus comprises a collapsible bag adapted for containing a liquid and a reusable support structure adapted for surrounding and supporting the collapsible bag. The apparatus may include an environmental containment enclosure surrounding at least a portion of the reusable support structure. A gap may be formed between an inner surface of the environmental containment enclosure and at least one of an outer surface of the reusable support structure and an outer surface of the collapsible bag, the gap defining an enclosed space which is not in continuous fluid communication with an interior portion of the collapsible bag. In some cases, the environmental containment enclosure is configured to maintain an aseptic and/or substantially particle-free environment within the enclosed space.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
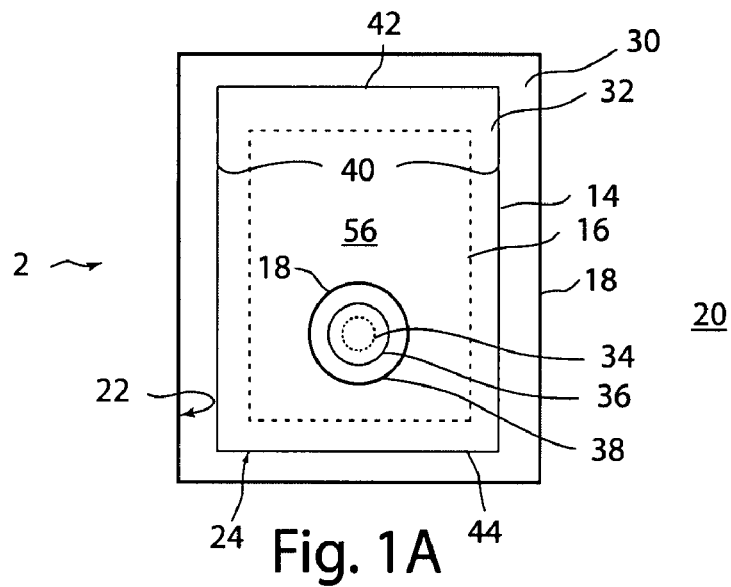
FIGS. 1A-1C are schematic diagrams showing side views of environmental containment systems, according to an embodiment of the invention.

The present invention relates in certain aspects to environmental containment systems, and in certain embodiments, to systems and methods involving vessels and unit operations or components of cell culture, cell containment, bioreactor, chemical manufacturing, or pharmaceutical manufacturing systems provided with environmental containment. Certain vessels, unit operations, devices, and/or components of the invention may be used to perform all or part of a biological, chemical, and/or pharmaceutical manufacturing process therein. In some embodiments, an inventive environmental containment system includes a multi-level containment apparatus. For instance, a first substantially closed environmental containment enclosure may be contained within a second substantially closed environmental containment enclosure; the first and second enclosures may be contained in a third substantially closed environmental containment enclosure, etc. Each of the environments within the substantially closed environmental containment enclosures may be controlled independently, and leakage of any materials from an inner system may be contained by an outer system.

In other embodiments, a vessel or other device or unit operation may have attached thereto an environmental containment enclosure which is part of an environmental containment system configured to maintain a sterile, aseptic, substantially particle-free, or reduced-particle environment within the enclosure. In certain embodiments, especially embodiments involving large vessels, the environmental containment enclosure has a shape and/or contour that is complementary to a shape and/or contour of a vessel to which the enclosure is attached to allow access to a material contained in the vessel from various locations around the vessel. The complementary shape and/or contour also reduces the overall size and/or footprint of the vessel and containment enclosure combination. In certain embodiments, access is achieved without subjecting the material to an external atmosphere surrounding the environmental containment enclosure(s). Accordingly, such environmental containment systems can prevent or decrease the amount of contamination, e.g., from personnel, equipment, and ambient air, of a material contained in the vessel or the degree of exposure of a user to the material. These systems may be particularly useful for producing and/or isolating toxins or other infectious materials within the vessel with improved safety.

The following documents are incorporated herein by reference in their entirety: U.S. Provisional Patent Application Ser. No. 60/903,977, filed Feb. 28, 2007, entitled "Weight Measurements of Liquids in Flexible Containers," by P. A. Mitchell, et al.; U.S. Provisional Patent Application Ser. No. 60/830,997, filed Jul. 14, 2006, entitled "Stirred Tank Bioreactor Having Environmental Containment," by G. Hodge, et al.; U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005; International Patent Application No. PCT/US2005/020083, filed Jun. 6, 2005, entitled "Disposable Bioreactor Systems and Methods," by G. Hodge, et al., published as WO 2005/118771 on Dec. 15, 2005; U.S. patent application Ser. No. 11/050,133, filed Feb. 3, 2005, entitled "System and Method for Manufacturing," by G. Hodge, et al., published as U.S. Patent Application Publication No. 2005/0226794 on Oct. 13, 2005; and International Patent Application No. PCT/US2005/002985, filed Feb. 3, 2005, entitled "System and Method for Manufacturing," by G. Hodge, et al., published as WO 2005/076093 on Aug. 18, 2005.

Although much of the description herein involves an exemplary application of the present invention related to bioreactors (and/or biochemical and chemical reaction systems including liquid-containing vessels), the invention and its uses are not so limited, and it should be understood that aspects of the invention can also be used in other settings, including those involving containment systems in general, systems for containment and/or processing of a fluid (e.g., a liquid or a gas) in a container (e.g., mixing systems), systems related to a biological, chemical, and/or pharmaceutical manufacturing process (e.g., primary recovery, filtration and chromatography systems, cell culture systems, microscopy and/or other analytical devices, etc.), as well as other applications that require sterile, aseptic, substantially particle-free, and/or reduced-particle environments. It should also be understood that while many examples provided herein involve the use of vessels comprising collapsible bags or flexible containers, aspects of the invention can be integrated with vessels comprising non-collapsible or rigid containers, and other configurations involving liquid containment.

In one aspect of the invention, an apparatus with environmental containment is provided. As shown in the embodiment illustrated in FIG. 1A, apparatus 2 includes a containment apparatus 14 which surrounds and contains a vessel, unit operation or other processing device or component thereof 16. In one embodiment, containment apparatus 14 is an environmental containment enclosure. An "environmental containment enclosure" as used herein refers to an enclosure at least partially surrounding and creating a substantially closed or closable space (an "enclosed space") having, when in operation, a sterile, aseptic, substantially particle-free, or reduced-particle environment inside the enclosure (as compared to an environment surrounding the enclosure). As described in more detail below, the containment apparatus may be in fluid communication with a ventilation system that helps to maintain such an environment inside the containment apparatus. The ventilation system may be external to the enclosure or could be partially or completely contained within the enclosure. Alternatively, instead of or in addition to a ventilation system, some other environmental treatment system may be used to create and maintain a sterile, aseptic, substantially particle-free, or reduced-particle environment, such as, for example, an ultraviolet and/or other form of radiation sterilizer, a source of steam, ethylene oxide and/or other disinfectant, etc.

In another embodiment, containment apparatus 14 is a vessel comprising a reusable support structure such as a stainless steel tank, and vessel 16 is a container adapted for containing a liquid (e.g., collapsible bag). In other embodiments, other vessel(s), unit operation(s), or other processing device(s) or component(s) thereof may be contained in apparatus 2. In general, for simplicity and conciseness, unless prohibited by the surrounding context, the term "vessel" may be used as a shorthand for indicating a volumetric container adapted for containing a liquid, a support structure for supporting a volumetric container, a unit operation component, or another device or component thereof forming at least part of a cell culture, cell containment, bioreactor, chemical manufacturing, pharmaceutical manufacturing, or other manufacturing system. For example, vessel 16 may be in the form of a unit operation component for performing a biological, chemical, and/or pharmaceutical manufacturing process. Non-limiting examples of unit operation components include stirred-tank bioreactors, filtration systems, seed culture expansion systems, primary recovery systems, chromatography systems, filling systems, closed media/buffer preparation systems, and water purification systems (e.g., water for injection (WFI) systems). As illustrated, an additional containment enclosure 18, which may be an environmental containment enclosure, may surround and contain both containment enclosure 14 and vessel 16.

As shown in the embodiment illustrated in FIG. 1A, environmental containment enclosure 18 surrounds containment apparatus 14 such that a gap 30 is formed between an inner surface 22 of the environmental containment enclosure and an outer surface 24 of the containment apparatus. This gap defines an enclosed space, at least a portion of which is positioned between containment apparatus 14 and environmental containment enclosure 18. Environmental containment enclosure 18 may be configured to maintain a sterile, aseptic, particle-free, or reduced-particle environment within this enclosed space. For instance, the environmental containment enclosure may be substantially closed off from atmosphere 20 to prevent particles or other materials in the atmosphere from entering gap 30. Additionally, an optional ventilation system or other environmental treatment system may be provided in fluid communication with the enclosed space defined by gap 30, e.g., to circulate filtered or otherwise treated gases into the enclosed space and/or to enable removal of gases from the enclosed space, as described below.

As illustrated, a gap 32 may be formed between containment apparatus 14 and vessel 16. In some embodiments, gap 32 defines an enclosed space between the containment apparatus 14 and the vessel 16. In embodiments where containment apparatus 14 is an environmental containment enclosure, a sterile, aseptic, particle-free, or reduced-particle environment is maintained within this enclosed space. If desired, a ventilation system or other environmental treatment system may be in fluid communication with gap 32, e.g., to circulate filtered or otherwise treated gases into the gap and/or to enable removal of gases from the gap. Alternatively, a portion of containment apparatus 14 may be open such that at least a portion of gap 32 is in continuous fluid communication with gap 30. In such embodiments, at least a portion of gap 30 is formed between an outer surface of vessel 16 and inner surface 22 of environmental containment enclosure 18.

In other embodiments, the enclosed spaces defined by gaps 30 and 32 are not in continuous fluid communication with each other as described above but rather are in controlled and/or intermittent fluid contact (i.e., restricted fluid communication) through an intermediate control valve, check valve, filter (e.g., a HEPA filter), combinations thereof or the like, enabling gas but not a substantial quantity of particles and/or undesirable agents to pass from one enclosure to the other. In yet other embodiments, the enclosed spaces defined by gaps 30 and 32 are not in fluid communication with one another.

In some embodiments, vessel 16 includes a sealable opening 34 (e.g., in the form of a septum or a valve) for accessing a material within the vessel. The containment apparatus may also include an access port 36, which may include, for example, an opening, a sealable port, a one-way valve, a two-way valve, a filter (e.g., a HEPA filter), or combinations thereof. Optionally, environmental containment enclosure 18 includes an access port 38, allowing access to a material in vessel 16 from an area outside of the environmental enclosure. Such an access port may be in the form of a glove access port or an iris port, for example. In some embodiments, an access port of the environmental containment enclosure is a door allowing a user to enter into the enclosed space (e.g., while wearing a soft-body suit or other suitable attire). By including an access port, a user can access a material contained in the vessel without subjecting the material to atmosphere 20 surrounding the outer-most environmental containment enclosure. Such a multi-leveled containment system can also protect the user from being exposed to the material contained within an inner containment apparatus, such as when hazardous materials are used. Additionally, the environment within one or more of the enclosures may be maintained at an appropriate environmental quality (e.g., Class 100, Class 1,000 or Class 10,000 environment), e.g., depending on the particular process to be performed in the vessel. It should be understood that although the environmental containment enclosure, containment apparatus, and vessel of FIGS. 1A-1C are each shown to have only one access port, in other embodiments each of the apparatuses includes a plurality of access ports, e.g., greater than 1, 2, 3, 4, 5, 8, 10, etc. access ports.

In other embodiments, environmental containment enclosure 18 does not include any access ports. This arrangement may be suitable when access to a material contained in an inner containment apparatus is not required. Or, in other cases, access to a material may be performed via a device, such as an automated sampler, positioned inside gap 30. For example, all or a portion of a sampling device can be positioned in gap 30 and may access a material within vessel 16 by opening sealable port 34 and/or by inserting a fluid transfer apparatus through port 34, e.g., which may be in the form of a septum. Thus, the material may be accessed and/or analyzed without opening the environmental containment enclosure.

Advantageously, apparatuses described herein (with or without access ports) may include multiple levels of containment such that if leakage occurs within an interior containment apparatus, the leakage will be contained within a second containment apparatus which contains the first apparatus. Additionally, if a third containment apparatus is used, the user may be further protected from exposure to the material in case leakage of the second containment apparatus occurs. Such systems are especially useful for containing toxins and other hazardous and/or infectious materials (e.g., Biosafety Level (BSL) 3 or 4 materials).

Figure 1B:
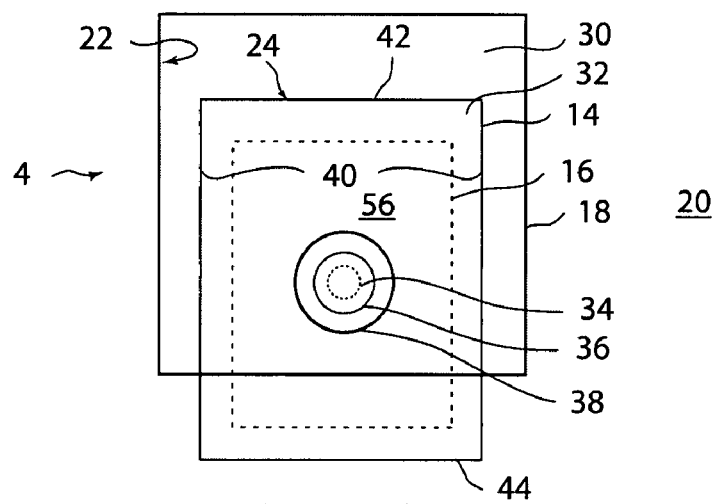
Figure 1C:
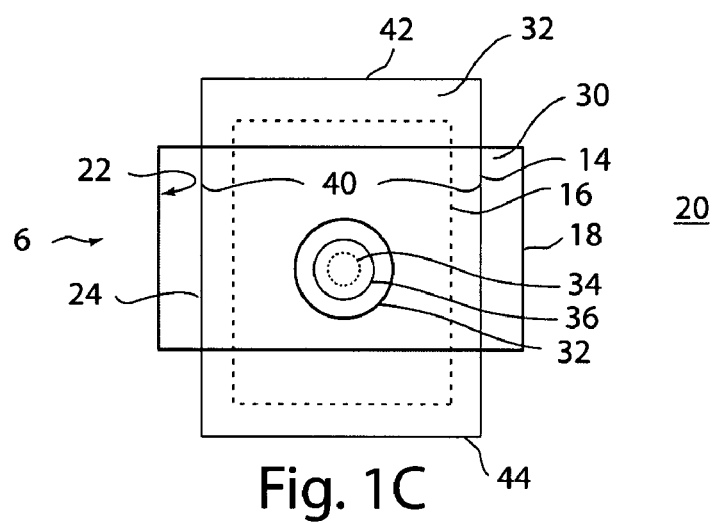

As previously mentioned, in some cases, the apparatuses shown in FIGS. 1A-1C are designed such that the enclosed space defined by gap 30 is not in continuous fluid communication with an interior portion of containment apparatus 14 and/or vessel 16. That is, although there may be a sealable port or other component interconnecting gap 30 and an interior portion of the containment apparatus 14 and/or vessel 16, where the port or component allows intermittent, selective or controlled transfer of fluid or materials between these areas, fluid is not continuously flowing or being transferred between the areas. In other cases, however, the apparatuses may be designed to allow continuous fluid communication between the enclosed space and an interior portion of the containment apparatus 14 and/or vessel 16. The direction of fluid flow may be controlled by inserting one-way valves between the containment apparatuses.

As mentioned, FIG. 1A includes an environmental containment enclosure 18 surrounding all of containment apparatus 14, including side portions 40, top portion 42, and bottom portion 44 of the containment apparatus. In other embodiments, an outer-most containment apparatus such as environmental containment enclosure 18 can surround a portion, but not all, of containment apparatus 14, as shown in the embodiments illustrated in FIGS. 1B and 1C. For instance, FIG. 1B shows environmental containment enclosure 18 surrounding a part, but not all, of side portions 40 and all of top portion 42, however, bottom portion 44 is exposed to atmosphere 20. Such an embodiment may be useful for systems that require direct access to a bottom portion of containment apparatus 14. For example, in one embodiment, an external device such as a motor of a mixing system is positioned at bottom portion 44. The external motor may be coupled (e.g., magnetically or mechanically) to an impeller positioned within vessel 16. By positioning the motor outside of the containment systems, the motor can be accessed easily by a user for maintenance, reconfiguration, inspection, and/or other purposes. This arrangement can also prevent or reduce contamination of the enclosed space defined by gap 30 with any particles, gases, or other materials that may be generated by operating and/or maintaining the external device.

In other cases, instead of environmental containment enclosure 18 surrounding top and side portions of containment apparatus 14, the enclosure surrounds the bottom and side portions of the containment apparatus. This configuration can facilitate access to the exposed top portion, including a motor or other component associated with the top portion.

Alternatively, as shown in the embodiment illustrated in FIG. 1C, apparatus 6 may include environmental containment enclosure 18 surrounding only parts of side portions 40 of containment apparatus 14, but not top portion 42 or bottom portion 44 of the apparatus. This configuration can allow a user to access the top and bottom portions of containment apparatus 14. For example, in some embodiments apparatus 6 may include a foam breaker positioned at a top portion of containment apparatus 14. The foam breaker may have an external motor positioned outside of the containment apparatus coupled (e.g., magnetically or mechanically) to an impeller positioned within vessel 16. The apparatus may also include a mixer positioned at the bottom portion, as described above.

It should be understood that other arrangements of containment apparatuses, vessels, and environmental containment enclosures are possible and that the invention is not limited in this respect. For instance, although one and, optionally, two environmental containment enclosures are shown in each of FIGS. 1A-1C, in other embodiments, an apparatus may include more than three environmental containment enclosures (e.g., greater than 3, 4, 5, 6, etc. environmental containment enclosures) that form an environmental containment system.

It should also be understood that the environmental containment enclosure, as well as any containment apparatuses contained therein, can have any suitable configuration which can vary depending on the intended use. For instance, in one embodiment, environmental containment enclosure 18, containment apparatus 14, and vessel 16 are all flexible structures such as collapsible bags that can be inflated with pressure. In another embodiment, each are rigid structures. In yet other embodiments, a combination of flexible and rigid structures can be used. Foldable structures such as structures having creases can also be incorporated in apparatuses and enclosures described herein. Flexible and/or foldable structures forming an environmental containment enclosure may be useful for forming large enclosures that allow a user to enter into the enclosed space (e.g., while wearing a soft-wall body suit or other suitable attire).

By way of example, in one particular embodiment, containment apparatus 14 is a vessel such as a reusable support structure for surrounding and supporting vessel 16, which may be a collapsible bag adapted for containing a liquid. In some cases, the reusable support structure includes at least one portion that is open, e.g., an open top portion which facilitates placement and/or removal of the collapsible bag into/from the support structure. In other cases, the reusable support structure is substantially closed during use and may include a door or other access port that can facilitate placement and/or removal of the collapsible bag. The environmental containment enclosure may surround at least a portion of the vessel, and, in some cases, the entire vessel as illustrated in FIG. 1A. The environmental containment enclosure may be configured to maintain an aseptic, particle-free, or reduced-particle environment within the enclosed space defined by gap 30 such that material withdrawn from the collapsible bag is kept uncontaminated within the enclosed space. Optionally, the apparatus may include a second environmental containment enclosure surrounding at least a portion of the first environmental containment enclosure. A second enclosed space may be defined between an inner surface of the second environmental containment enclosure and an outer surface of the first environmental containment enclosure. The second environmental containment enclosure may be configured such that the second enclosed space is not in continuous fluid communication with an interior portion of the vessel.

It should be understood that a variety of vessels, such as stirred-tank bioreactors, and vessels in the form of filtration systems, seed culture expansion systems, primary recovery systems, chromatography systems, filling systems, closed media/buffer preparation systems, and water purification systems (e.g., water for injection systems) can include environmental containment enclosures, and can be configured as illustrated in FIGS. 1A-2C and/or as described herein.

Figure 2A:
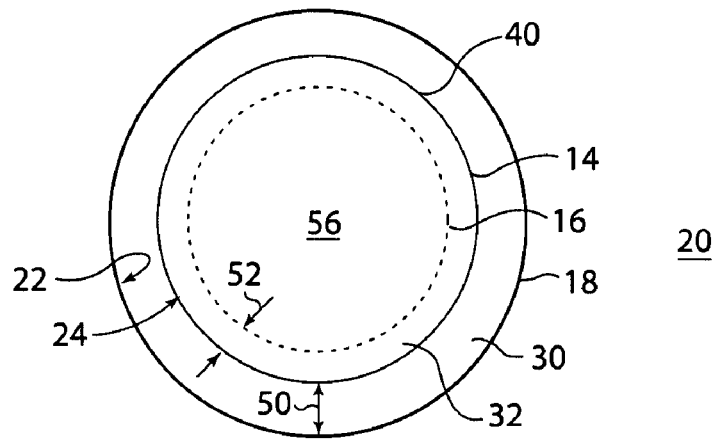
FIGS. 2A-2C are schematic diagrams showing top views of environmental containment systems, according to an embodiment of the invention.
Figure 2B:
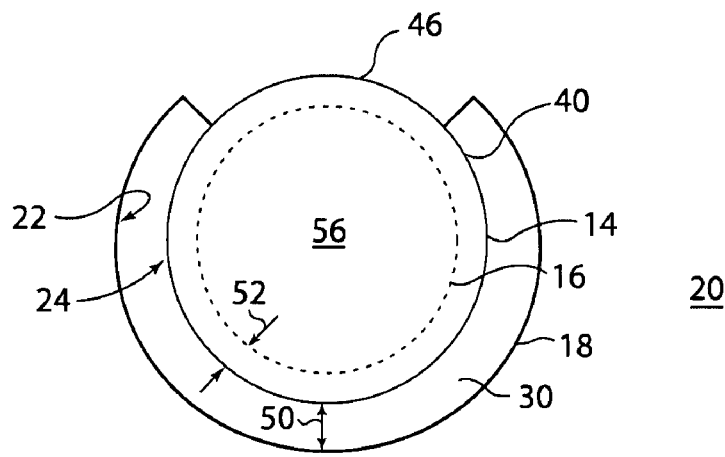
Figure 2C:
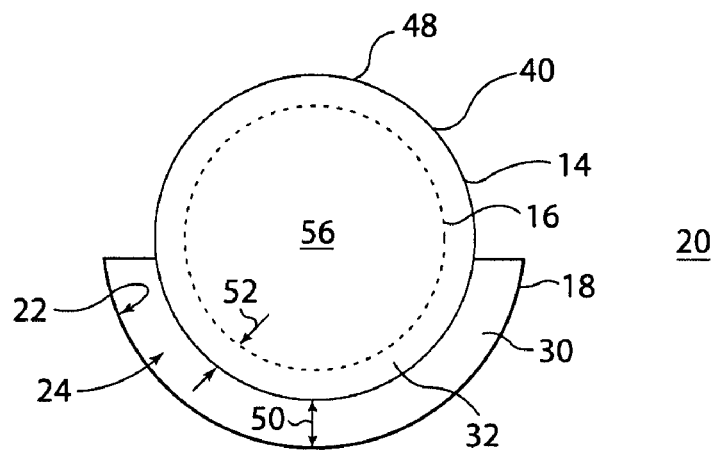

FIGS. 2A-2C show top views of exemplary embodiments of apparatuses such as the ones illustrated in FIGS. 1A-1C. It should be understood that each of FIGS. 2A-2C may represent top views of any of the apparatuses shown in FIGS. 1A-1C. For instance, FIG. 2A shows enviromental containment enclosure 18 surrounding all of side portions 40 of containment apparatus 14. In some cases, the top and bottom portions of containment apparatus 14 are surrounded by environmental containment enclosure 18, as shown in FIG. 1A. In other embodiments, however, FIG. 2A corresponds to an apparatus where environmental containment enclosure 18 surrounds all of side portions 40 and a top portion of the apparatus, but not a bottom portion of the apparatus, as depicted in FIG. 1B. In yet other embodiments, FIG. 2A corresponds to an apparatus where environmental containment enclosure 18 surrounds all of the side portions, but not the top or bottom portions of the apparatus, as shown in FIG. 1C.

FIGS. 2B and 2C illustrate apparatuses where only parts, but not all, of side portions 40 of containment apparatus 14 are surrounded by environmental containment enclosure 18. Such embodiments may be useful for apparatuses that require direct access to side portions of the containment apparatus 14. For instance, the containment apparatus may include a component such as a door, exhaust, and/or electrical equipment positioned at side portions 46 or 48, which are not surrounded by environmental containment enclosure 18. Any openings associated with these components may be sealed (e.g., hermetically) so as to form a substantially closed system within containment apparatus 14 during use (e.g., sufficiently closed to enable a sterile, aseptic, particle-free, or reduced-particle environment to be maintained). Additionally and/or alternatively, components external to containment apparatus 14, such as a heat deflector or a structure mechanically supporting the apparatus, may be positioned at or near side portions 46 or 48.

As shown FIGS. 1A-2C, the apparatuses may include an environmental containment enclosure 18 having a shape and/or contour that is complementary to an outer surface 24 of containment apparatus 14 (e.g., a vessel in the form of a unit operation component for performing a biological, chemical, and/or pharmaceutical manufacturing process) to which the environmental containment enclosure is adjacent. In certain embodiments, as shown in FIGS. 2A-2C, the environmental containment enclosure has a curved shape that is complementary to a curved shape of the outer surface of the containment apparatus 14. By designing the environmental enclosure to have a complementary shape and/or contour, a user can easily access an inner containment apparatus from one or more directions, while maintaining a sterile, aseptic, particle-free, or reduced-particle environment within the enclosed space defined by gap 30. The size and footprint of the overall apparatus can also be reduced. For instance, a complementary shaped and/or contoured environmental containment enclosure can facilitate access to an inner containment apparatus having ports or other components located at different positions around the apparatus. This arrangement is particularly useful for inner containment apparatuses having large surface areas, where access to different positions around the apparatus would otherwise be difficult. Furthermore, all or portions of an environmental containment enclosure may be transparent to allow visual access to an inner containment apparatus.

The environmental containment enclosure may have any suitable dimensions, which may depend on factors such as the size of an inner containment apparatus, the types and configurations of access ports, and properties of the materials (e.g., Biosafety Level 1, 2, 3, or 4) to be processed in an inner containment apparatus. As an environmental containment enclosure may be adapted to enable a user standing outside of the enclosure to access an inner containment apparatus, the distance between inner surface 22 of the environmental containment enclosure and outer surface 24 of the containment apparatus may be on the order of a user's working distance. For instance, referring to FIGS. 2A-2C, an average distance 50 between inner surface 22 of the environmental containment enclosure and outer surface 24 of the containment apparatus may be, for example, less than 1 meter (m), or, in other embodiments, less than 0.7 m, 0.5 m, 0.3 m, or 0.1 m. In some cases, average distance 50 is between 0.05-1 m, 0.2-1 m, 0.2-0.5 m, or 0.5-1 m. Smaller average distances 50 can reduce the volume within the enclosed space, thereby reducing the amount of gases that may be required to circulate and/or filtered within the enclosed space. In such embodiments, smaller ventilation systems can also be used.

In other embodiments, average distance 50 may be greater than 1 m, such as embodiments where a user can access an inner containment apparatus indirectly, e.g., via a robotic arm or the like. In yet other embodiments, the environmental containment enclosure is designed to allow a user to walk into the enclosed space defined by the enclosure. As such, average distance may be, for example, between 1-2 m, 1-4 m, or 1m, or 1 -6 m.

As average distance 50 may vary depending on the size of a containment apparatus to which it is immediately adjacent, the ratio of the average diameter of the containment apparatus to average distance 50 may be, for example, less than 20:1, or, in other embodiments, less than 15:1, 10:1, 8:1, 5:1, 3:1, 2:1, 1:1, 0.5:1, 0.3:1, or 0.1:1.

The volume within an environmental containment enclosure (e.g., defined by gap 30 or 32) may also vary depending on the size of a containment apparatus to which it is immediately adjacent. As such, the volume within an environmental containment enclosure may be, for example, between 1-100 liters (L), 100-200 L, 200-300 L, 300-500 L, 500-750 L, 750-1,000 L, 1,000-2,000 L, 2,000-5,000 L, or 5,000-10,000 L. In some instances, an environmental containment enclosure has a relatively large volume, e.g., greater than 1 L, or in other instances, greater than 10 L, 20 L, 40 L, 100 L, 200 L, 500 L, or 1,000 L. Volumes greater than 10,000 L are also possible. In other embodiments, an environmental containment enclosure has a relatively small volume, e.g., less than 10,000 L, or in other cases, less than 1,000 L, 500 L, 200 L, 100 L, 40 L, 10 L, or 1 L.

The environmental containment enclosure and containment apparatuses may be associated with one another in any suitable manner. For instance, in some cases, the environmental containment enclosure is irreversibly attached to containment apparatus 14, which may be, for example, a vessel comprising a container for containing a liquid, optionally comprising or in the form of a unit operation component for performing a biological, chemical and/or pharmaceutical process. Similarly, in embodiments where containment apparatus 14 is an environmental containment enclosure, containment apparatus 14 may be irreversibly attached to vessel 16. In some such embodiments, environmental containment enclosure 18 is omitted. In certain such embodiments, containment apparatus 14 surrounds only a portion of vessel 16 rather than the entirety of vessel 16 as illustrated.

In one particular embodiment, containment apparatus 14 includes one or more flanges that protrude from side portions of the containment apparatus to which portions of the environmental containment enclosure can be fastened. As used herein, the term "irreversibly attached," when referring to two or more objects, means separation of the two or more objects requires causing damage to at least one of the object (or components of the object), for example, by breaking or peeling (e.g., separating components fastened together via adhesives, tools, etc.). In other embodiments, the environmental containment enclosure is reversibly attached to the containment apparatus (i.e., able to be separated by hand or with tools without damage to the components).

In certain embodiments in which the environment containment enclosure is irreversibly (or reversibly) attached to an immediately adjacent containment apparatus, the environmental containment enclosure is specifically designed and configured to operate with that particular containment apparatus. For instance, depending on the function of the containment apparatus, which may include or be, for example, a vessel comprising a stirred-tank bioreactor, a filtration system, a seed culture expansion system, a primary recovery system, a chromatography system, a filling system, a closed media/buffer preparation system, or a water purification system, the environmental containment enclosure may have different dimensions, numbers and types of access ports, environmental control, ventilation systems, and the like. Thus, unlike an environmental containment system that includes simply an empty space for inserting a vessel or other system (e.g., a system where a vessel is unattached and merely inserted into an environmental containment enclosure), attached environmental containment enclosures of the invention may be tailored to a particular containment apparatus/vessel for performing a specific process. This design can allow the environmental containment enclosure and containment apparatus to be pre-configured, e.g., with complementary dimensions, ports, control systems, and the like, so that a user can use the apparatus to perform an operation with simplified assembly and/or setup. Furthermore, in situations where an apparatus including an environment containment enclosure is tailored to perform a specific process at a first location, and then the apparatus is shipped to a second location to perform the same process, a user at the second location can begin operating the apparatus quickly without having spent much time understanding how to assemble and/or operate the system. This approach can also increase the chances of operating the process efficiently and correctly at the second location, as the apparatus has already been tested at the first location.

In addition, any inner containment apparatuses such as containment apparatus 14 and vessel 16 may be associated with each other in any suitable manner. For example, in certain cases where vessel 16 is a collapsible bag, the collapsible bag may be surrounded and reversibly contained within containment apparatus 14 (e.g., which may be in the form of a rigid support vessel) such that after a process has been performed inside the collapsible bag, the bag can be removed from the system. In another example, a vessel, e.g., in the form of a unit operation component, may simply be placed in the containment apparatus without reversible or irreversible attachment. In other embodiments, vessel 16 and containment apparatus 14 can be irreversibly or reversibly attached to one another.

Each of the apparatuses shown in FIGS. 1A-2C may be operated under different environmental conditions to produce a sterile, aseptic, and/or substantially particle-free environment within one or more of the environmental containment enclosures. For example, in one embodiment, interior 56 of vessel 16 is operated at a first pressure greater than atmospheric pressure (e.g., atmosphere 20). Containment apparatus 14 and, therefore, gap 32, may be operated at a second pressure less than the first pressure. In some cases, a ventilation system is in fluid communication with gap 32, which can facilitate removal of a gas or particles from, and/or introduction of a gas into, gap 32. Because of the differences in pressure between interior 56 and gap 32, gas flow from the interior to the gap is favored, and any gases or materials that may escape from the interior can be removed by the ventilation system. Additionally, gap 30 may be operated at a third pressure greater than the second pressure within gap 32. This system can allow any gases or materials that enter gap 32 from gap 30 to be removed by the ventilation system. The third pressure in gap 30 may optionally be greater than atmospheric pressure and, in some such embodiments, access ports associated with environmental containment enclosure 18 may include apertures that allow gases within gap 30 to leak out of the apertures into atmosphere 20. This constant flow of gas from the enclosed space into the atmosphere can reduce the amount of gases or materials in atmosphere 20 from entering the enclosed space defined by gap 30. Additionally and/or alternatively, a ventilation system (the same or different from the ventilation system in fluid communication with gap 32) may be in fluid communication with gap 30. It should be understood that environmental containment enclosures can be operated under other conditions that may produce a sterile, aseptic, substantially particle-free, or reduced particle environment within one or more of the enclosed spaces. For example, relative pressures can be adjusted depending on the number of environmental containment enclosures, the nature of the material within a vessel, and/or the degree of sterility of the ambient atmosphere in which the apparatus is positioned.

By including environmental containment for apparatuses described herein, integrity and control of the environment inside the apparatus can be achieved for one or more steps of a manufacturing process. Accordingly, in some embodiments, apparatuses may be used in an unclassified ambient space, thereby saving costs associated with otherwise forming and/or maintaining a clean room facility. Additionally, environmental conditions within the apparatuses may be classified in a manner consistent with normal process suite classifications for typical manufacturing systems. For example, an apparatus used for bioreactor fermentation may be operated as unclassified, while apparatuses designed for purification may be classified as Class 10,000. Seed and bulk drug substance fill apparatus environments may be classified as Class 100 environments. Those of ordinary skill in the art can determine the appropriate environments required for performing particular biological, chemical, and/or pharmaceutical manufacturing processes.

In addition, one or more of the following exemplary attributes may contribute to control of an environment within an apparatus: substantially closed apparatuses in which manual operations are conducted through glove and/or iris ports; individual, segregated ventilation systems that provide one pass, HEPA filtered air to the apparatus or a common ventilation system associated with each of the apparatuses if more than one apparatus is used; operation of the apparatus under positive pressure during manufacturing, operation and/or cleaning; control, measurement and/or continual monitoring of temperature, humidity, airflow and particulates; routine environmental monitoring program that includes automated, continuous, on-line monitoring of apparatuses during manufacturing for total particulates with alarms for out-of-tolerance events; routine sampling of classified apparatuses for viable particulates in accordance with industry standards for controlled environments; limited access to a common manufacturing space with separate entry and exit paths; gowning of personnel entering the common manufacturing space including lab coats, boots, bouffant hair covers, gloves and safety goggles; materials transported into or out of common manufacturing space in sealed containers; surfaces cleaned (e.g., wiped or sprayed) with sanitizing agent before entering manufacturing area; removal of final bulk product or intermediate in sealed containers in a controlled environment; liquid process waste inactivation prior to removing from an apparatus; solid waste removed in a sealed bag; apparatuses designed for containment of large spills and inactivation of spill before removal via a substantially closed system; procedures for abnormal events similar to those used in traditional facilities; validated cleaning procedures executed with verification step in electronic batch record steps; clean status requires completion of procedure, including appropriate environmental monitoring; clean status of apparatuses tracked by electronic documentation system; "clean" status required in order for an apparatus to be assigned to a batch; validation of apparatus integrity and ventilation system under static and dynamic conditions of normal use and abnormal events such as spills or power failures; cleaning validations support and substantiated apparatus cleaning procedures; multi-use equipment/process component cleaning procedures, etc.

Furthermore, in some embodiments, an environmental treatment system comprising an in-situ decontamination system may be associated with a containment apparatus (e.g., an environmental containment enclosure) for cleaning an interior of the apparatus and/or for maintaining a sterile, aseptic, substantially particle-free, or reduced-particle environment within the apparatus. The environmental treatment system may include or be in communication with a sensor or detector that determines (e.g., detects, measures, etc.) certain materials (e.g., particulates, particular chemical and/or biological species, etc.) in an enclosed space. For instance, a nozzle in fluid communication with a source of steam or a decontamination agent may be activated upon detection of a certain level of materials (e.g., particulates) within the enclosure or at the end of performing a manufacturing process. Non-limiting examples of decontamination agents include alcohols (e.g., ethanol and isopropanol), aldehydes (e.g., glutaraldehyde), haolgens (e.g., chloramine, chlorine, hypochlorites (e.g., bleach), and iodine), oxidizing agents (e.g., chlorine dioxide, hydrogen peroxide, ozone, peracetic acid, potassium permanganate, and potassium peroxymonosulfate), phenolics (e.g., phenol, O-phenylphenol, chloroxylenol, hexachlorphene, and thymol), and quaternary ammoniumm compounds (e.g., benzalkonium chloride). In other embodiments, an environmental treatment system includes an ultraviolet and/or other form of radiation sterilizer. One or more filters (e.g., gas filters) external or internal to an environmental containment enclosure can also be used. In some cases, combinations of the above-mentioned systems can be implemented. For instance, a first environmental containment enclosure may include a first environmental treatment system associated therewith, and a second environmental containment enclosure may include a second environmental treatment system associated therewith, where the first and second environmental treatment systems may be the same or different.

Figure 3:
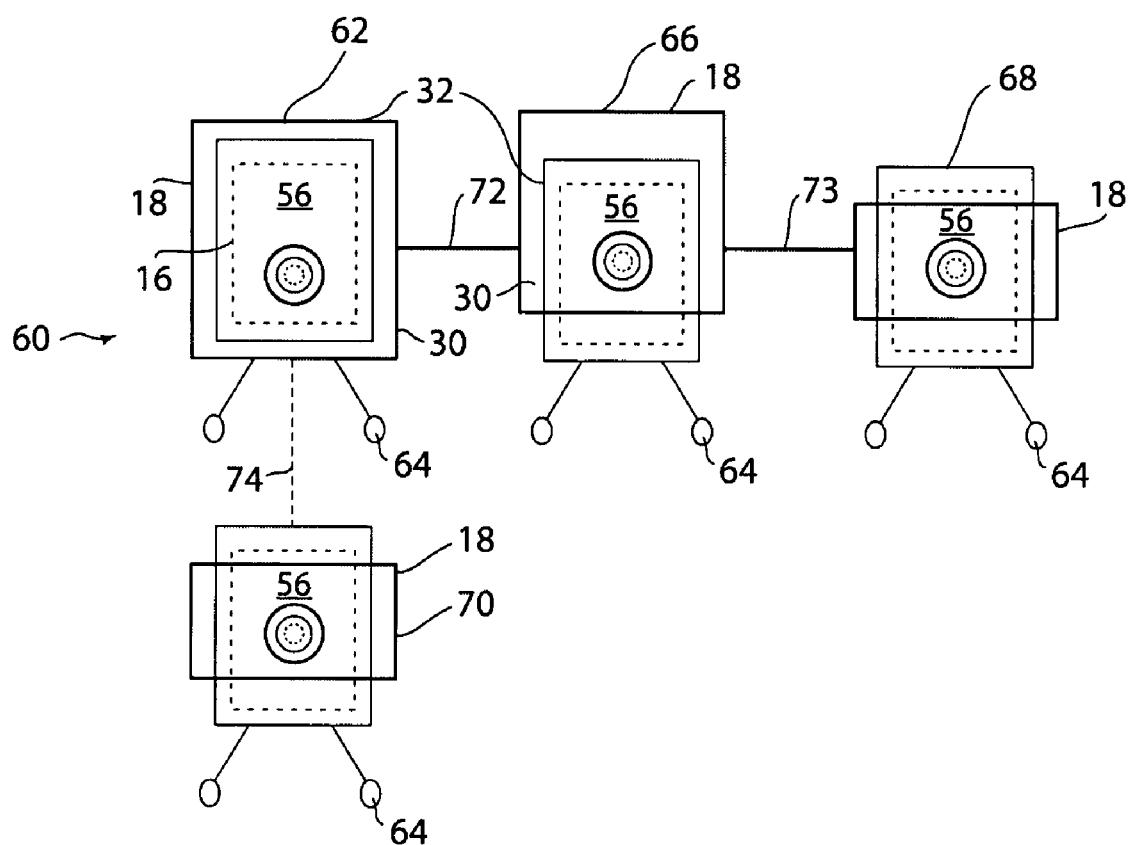
FIG. 3 is a schematic diagram showing interconnection of several environmental containment systems, according to an embodiment of the invention.

In some embodiments of the invention, apparatuses described herein are configured as individual mobile modules that can be interconnected with other modules to perform a series of steps relating to a biological, chemical, and/or pharmaceutical (e.g., biopharmaceutical) manufacturing process. For instance, as shown in the embodiment illustrated in FIG. 3, system 60 includes a first apparatus 62 having wheels 64 or other components for facilitating movement and/or portability of the apparatus. In some embodiments, each of the apparatuses includes a separate ventilation system; in other embodiments, a common ventilation system is associated with each of the apparatuses. In yet other embodiments, other types of environmental treatment systems can be used. Optionally, the first apparatus can be connected to second apparatus 66 via connection 72. Interconnection between apparatuses and methods associated therewith are described in more detail in U.S. patent application Ser. No. 11/050,133, filed Feb. 3, 2005, entitled "System and Method for Manufacturing," by G. Hodge, et al., published as U.S. Patent Application Publication No. 2005/0226794 on Oct. 13, 2005 and International Patent Application No. PCT/US2005/002985, filed Feb. 3, 2005, entitled "System and Method for Manufacturing," by G. Hodge, et al., published as WO 2005/076093 on Aug. 18, 2005, both of which are incorporated herein by reference.

Connection between apparatuses may take place through a variety of means such as, for example, a rigid or flexible tube, a latch, or the like. In some instances, a flexible connection between the apparatuses is formed, allowing each of the apparatuses to be moved in different orientations with respect to one another even when interconnected. This feature can facilitate transport of the apparatuses, especially around tight corners.

Connection between apparatuses 62 and 66 can be formed before, during, and/or after a process has been performed in first apparatus 62. In some embodiments, connection 72 allows fluid communication between gaps 30 of the apparatuses. In certain of these or other embodiments, connection 72 allows fluid communication between gaps 32 of the first and second apparatuses. In certain of these or yet other embodiments, connection 72 allows fluid communication between interiors 56 of the first and second apparatuses. This latter arrangement can allow, in some embodiments, a material within interior 56 of apparatus 62 to be transferred to an interior portion of apparatus 66. In some instances, combinations of the above can be achieved, as connection 72 can allow fluid communication between more than one interiors within the apparatuses. Optionally, the apparatuses can be connected physically but without fluid communication between interiors of the apparatuses.

Transfer of a material from apparatus 62 to apparatus 66 can allow the material to be further processed or manipulated in apparatus 66, which may have a different functionality than that of apparatus 62 (e.g., a different unit operation component). For instance, while apparatus 62 may include a vessel in the form of a reactor for producing a biological, chemical and/or pharmaceutical material, apparatus 66 may include a vessel configured to purify the material formed in apparatus 62. Because each of the apparatuses may be designed and configured specifically for carrying out a particular process, apparatuses 62 and 66 may have different configurations of environmental containment enclosures 18, as shown illustratively in FIG. 3.

If further processing or manipulation of the material within interior 56 of apparatus 66 is required, apparatus 66 can be interconnected with apparatus 68 via connection 73 in a manner described above in connection with apparatuses 62 and 66. Apparatus 68 may be designed and configured to perform a different process than that of apparatus 66; for instance, apparatus 66 may include a vessel comprising an ultra filtration system. Of course, additional apparatuses can be interconnected for performing further processing functions.

Advantageously, apparatuses that are configured to be individually mobile can be reconfigured after use to perform a second biological, chemical, or pharmaceutical process within the apparatus. For instance, after a material within apparatus 62 has been transferred to apparatus 66, apparatuses 62 and 66 can be disconnected and apparatus 62 can be used to perform a second process. In some cases, the second process is unrelated to the first process; for example, the first process may be forming a drug and the second process may be harvesting cells. In other cases, the second process is related to the first process; for example, the first process may be forming a drug precursor and the second process may be reacting the drug precursor with a compound to form a drug.

The use of disposable components within the apparatuses may facilitate reconfiguration of the apparatuses. For example, in one particular embodiment, apparatus 62 includes a vessel 16, which may be in the form of a disposable, collapsible bag that can be used as a biological, chemical, or pharmaceutical reaction vessel. After a first process has been performed in the disposable bag, and the material has been transferred from apparatus 62 to apparatus 66, the disposable bag can be removed from apparatus 62 and a new disposable bag can be inserted therein. This arrangement can allow a second process to be performed within apparatus 62 while the transferred material is processed in apparatus 66. Likewise, after the second process within apparatus 62 has been accomplished, the material within the apparatus can be transferred to apparatus 66. Alternatively, apparatus 62 can be interconnected with apparatus 70 via connection 74. Accordingly, one or more processes can be performed simultaneously using system 60, saving the user time and space.

As mentioned, apparatuses comprising environmental containment systems described herein may be self-sufficient and independently customized to perform a specific biological, chemical, or pharmaceutical process. This can allow, for example, system 60 to be customized to perform a particular process at a first location, disassembled, and then shipped to a second location to perform the same process at the second location. Because each apparatus may be mobile and independently operated, time and expertise required to assemble the apparatuses at the second location may be minimal. Automation of the apparatuses can also facilitate setup and use of the apparatuses at the second location, especially when users at the second location are untrained or unfamiliar with the system. Furthermore, the use of apparatuses having an environmental containment enclosure can allow the apparatuses to be used in non-sterile or non-clean room environments for processes requiring such environments, since the enclosed space(s) formed by the environmental containment enclosure(s) can be operated under sterile, aseptic, particle-free, or reduced-particle conditions. This feature can substantially save costs as clean room or other facilities may not be required.

In certain embodiments, vessels described herein are a part of a bioreactor system. Bioreactors may be used to produce a variety of products from various organisms such as, for example, bacteria, insects/insect cells, fungi, mammalian cells, human cells, yeast, shrimp, fish, protozoa, nematodes, viruses, algae, and higher plants/plant cells. A non-limiting example of an inventive bioreactor system including a container, such as a flexible container, and an environmental containment enclosure is shown in the schematic diagram of FIG. 4. As shown in the embodiment illustrated in FIG. 4, apparatus 100 includes a first containment apparatus in the form of a vessel 114, which, in the illustrated embodiment, is a reusable support structure (e.g., a stainless steel tank) that surrounds and contains a container 118. Apparatus 100 also includes a second containment apparatus in the form of an environmental containment enclosure 120, which surrounds a portion of vessel 114.

In some embodiments, container 118 is configured as a collapsible bag (e.g., a polymeric bag). Additionally or alternatively, all or portions of the collapsible bag or other container may be formed of a substantially rigid material such as a rigid polymer, metal, and/or glass. In other embodiments, a rigid container is used in this configuration, wherein inner walls of vessel 114 are in direct contact with the liquid, and container 118 is not present. Container 118 may be disposable and may be configured to be easily removable from support structure 114. In some embodiments, container 118 is reversibly attached to support structure 114 as previously described.

If a collapsible bag is used, collapsible bag 118 may be fluid tight to enable it to contain a liquid 122, which may contain reactants, media, and/or other components necessary for carrying out a desired process such as a chemical, biochemical and/or biological reaction. Collapsible bag 118 may also be configured such that liquid 122 remains substantially in contact only with the collapsible bag during use and is not in contact with support vessel 114. In such embodiments, the bag may be disposable and used for a single reaction or a single series of reactions, after which the bag is discarded. Because the liquid in the collapsible bag in such embodiments does not come into contact with support structure 114, the support structure can be reused without cleaning. That is, after a reaction takes place in container 118, the container can be removed from support structure 114 and replaced by a second (e.g., disposable) container. A second reaction can be carried out in the second container without having to clean either the first container or the reusable support structure.

Figure 4:
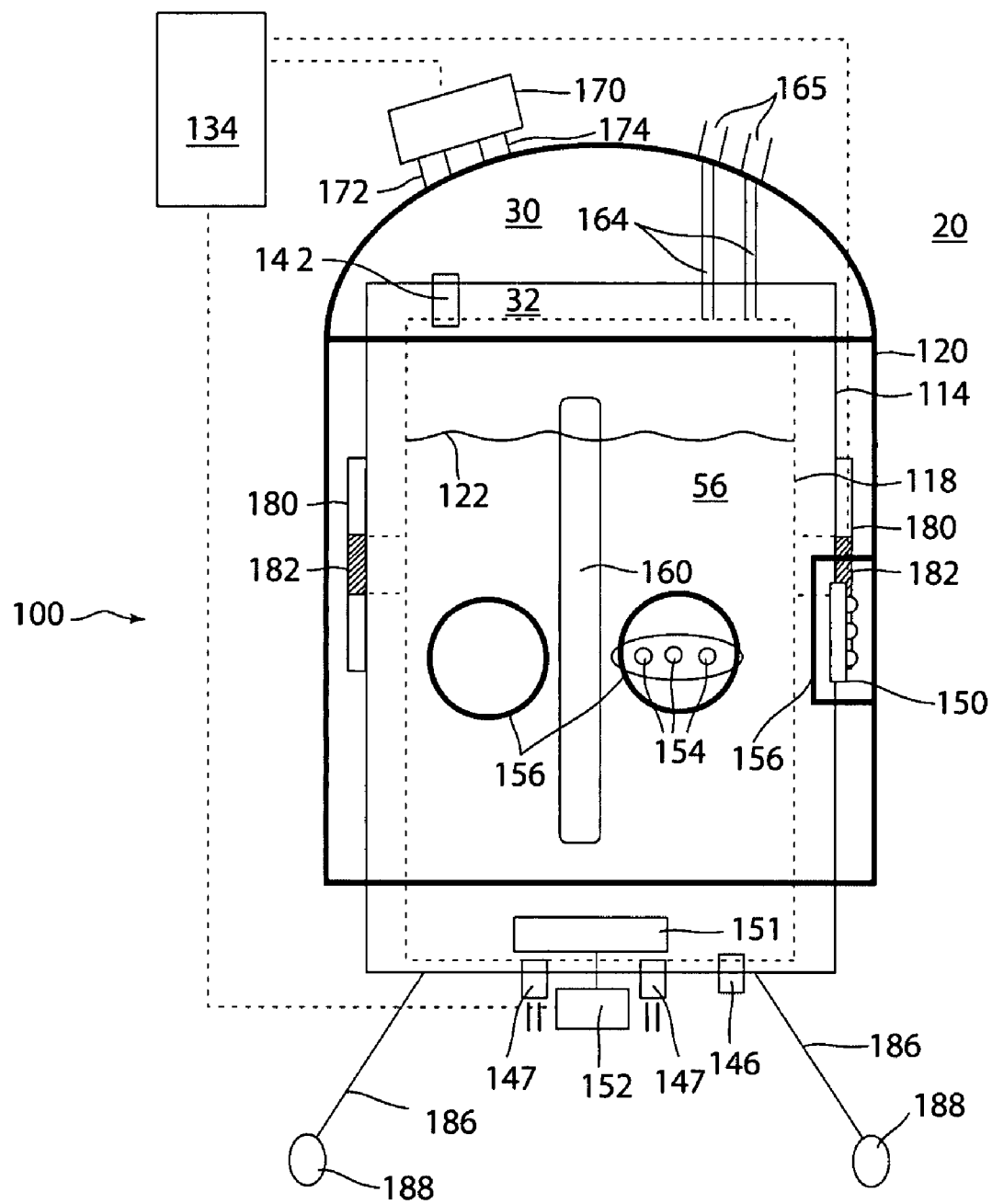
FIG. 4 is a schematic diagram showing a bioreactor provided with an environmental containment enclosure, according to an embodiment of the invention.

Also shown in FIG. 4 are an optional inlet port 142 and optional outlet port 146, which can be formed in container 118 and/or reusable support structure 114 and can facilitate more convenient introduction and removal of a liquid and/or gas from the container. The container may have any suitable number of inlet ports and any suitable number of outlet ports. For example, a plurality of inlet ports may be used to provide different gas compositions (e.g., via a plurality of spargers 147), and/or to allow separation of gases prior to their introduction into the container. These ports may be positioned in any suitable location with respect to container 118. For instance, for certain apparatuses including spargers, the container may include one more gas inlet ports located at a bottom portion of the container. Tubing may be connected to the inlet and/or outlet ports to form, e.g., delivery and harvest lines, respectively, for introducing and removing liquid from the container. Optionally, the container and/or support structure may include a utility tower 150, which may be provided to facilitate interconnection of one or more devices internal to the container and/or support structure with one or more pumps, controllers, and/or electronics (e.g., sensor electronics, electronic interfaces, and pressurized gas controllers) or other devices. Such devices may be controlled using a control system 134.

For systems including multiple spargers, control system 134 may be operatively associated with each of the spargers and configured to operate the spargers independently of each other. This can allow, for example, control of multiple gases being introduced into the container. In general, as used herein, a component of a system that is "operatively associated with" one or more other components indicates that such components are directly connected to each other, in direct physical contact with each other without being connected or attached to each other, or are not directly connected to each other or in contact with each other, but are mechanically, magnetically, electrically (including via electromagnetic signals transmitted through space), or fluidically interconnected so as to cause or enable the components so associated to perform their intended functionality.

Apparatus 100 may optionally include a mixing system such as an impeller 151 positioned within container 118, which can be rotated (e.g., about a single axis) using a motor 152 that may be external to the container. In some embodiments, as described in more detail below, the impeller and motor are magnetically coupled. The mixing system can be controlled by control system 134. Mixing systems are described in further detail below.

Additionally and/or alternatively, the apparatus may include an antifoaming system such as a mechanical antifoaming device (not shown). The antifoaming device may include, for example, an impeller within container 118 positioned near the top of the container that can be rotated (e.g., magnetically) using a motor, which may be external or internal to the container. The impeller can be used to collapse a foam contained in a head space of the container. In some embodiments, the antifoaming system is in electrical communication with a sensor (e.g., a foam sensor) via a control system. The sensor may determine, for instance, the level or amount of foam in the head space or the pressure in the container, which can trigger regulation or control of the antifoaming system. In other embodiments, the antifoaming system is operated independently of any sensors. Antifoaming systems are described in more detail in a PCT Application entitled, "Gas Delivery Configurations, Foam Control Systems, and Bag Molding Methods and Articles for Collapsible Bag Vessels," filed on Jun. 15, 2007, which is incorporated herein by reference.

Support structure 114 and/or container 118 may also include, in some embodiments, one or more ports 154 that can be used for sampling, analyzing (e.g., determining pH and/or amount of dissolved gases in the liquid), or for other purposes. These ports may be aligned with one or more access ports 156 of environmental containment enclosure 120. As shown in the illustrative embodiment, the environmental containment enclosure has a shape and contour that is complementary to a shape and contour of support structure 114 to which the enclosure is attached to allow access to a material contained in the container from various locations around the container. A complementary shaped and contoured environmental containment enclosure can also reduce the overall size and/or footprint of the support structure, container, and environmental containment enclosure combination. This feature is especially well-suited for large containers, where access to ports and/or other components around support structure 114 and/or container 118 may be otherwise difficult. Thus, a user positioned outside of the environmental containment enclosure can access a material within the container via the ports without subjecting the material to an atmosphere 20 surrounding the enclosure. The environmental containment enclosure can prevent or decrease the amount of contamination, e.g., from personnel, equipment, and ambient air, of a material contained in the system and/or the degree of exposure of the material to a user.

As shown, support structure 114 may also include one or more site windows 160 for viewing a level of liquid within the container 118. Alternatively, reusable support structure 114 may be formed of a transparent material to allow visual access into container 118. Environmental containment enclosure 120 may also be formed of a transparent material to allow visual access into the enclosure.

One or more connections 164 may be positioned at a top portion of container 118 or at any other suitable location. Connections 164 may include openings, tubes, and/or valves for adding or withdrawing liquids, gases, and the like from container 118, each of which may optionally include a flow sensor and/or filter (not shown). Optionally, connections 164 may be in fluid communication with gas introduction and withdrawl ports 165.

In some embodiments, one or more connections 172 and 174 may be positioned at a top portion of the environmental containment enclosure 120 or at any other suitable location. Connections 172 and 174 may include openings, tubes, and/or valves for adding or withdrawing gases and the like from the environmental containment enclosure 120, each of which may optionally include a flow sensor and/or filter (not shown). Optionally, connections 172 and 174 can be connected to a ventilation system 170 and may be in fluid communication with the enclosed space defined by gap 30. For instance, connection 172 may be a gas inlet for introducing a gas into the enclosed space and connection 174 may be a gas outlet for removal of a gas from the enclosed space. Ventilation system 170 may include filters (e.g. HEPA filters) and can be configured and operated, under control of control system 134, to create and maintain a sterile, aseptic, substantially particle-free, or reduced-particle environment.

Apparatus 100 may include, in some embodiments, one or more connection ports 180 for interconnecting an interior of reusable support structure 114 (e.g., gap 32) to an interior of a second apparatus. Additionally or alternatively, the apparatus may include one or more connection ports 182 adapted for connecting an interior of container 118 (e.g., interior 56) to an interior of an interior of the second apparatus. These ports can facilitate transfer of a material from interior 56 to the second apparatus or to another suitable container (e.g., a sealed bag). Transfer may be accomplished, for example, by pumping the material through tubing, by use of gravity, and/or by application of a vacuum. In some embodiments, this transfer can be performed without fluidically interconnecting an interior of reusable support 114 structure or an interior of the environmental containment enclosure 120 with another structure.

The support structure 114 may further include a plurality of supports 186, optionally with wheels 188 for facilitating transport of the apparatus.

It should be understood that not all of the features shown in FIG. 4 need be present in all embodiments of the invention and that the illustrated elements may be otherwise positioned or configured. Also, additional elements may be present in other embodiments, such as the elements described in more detail below.

Figure 5:
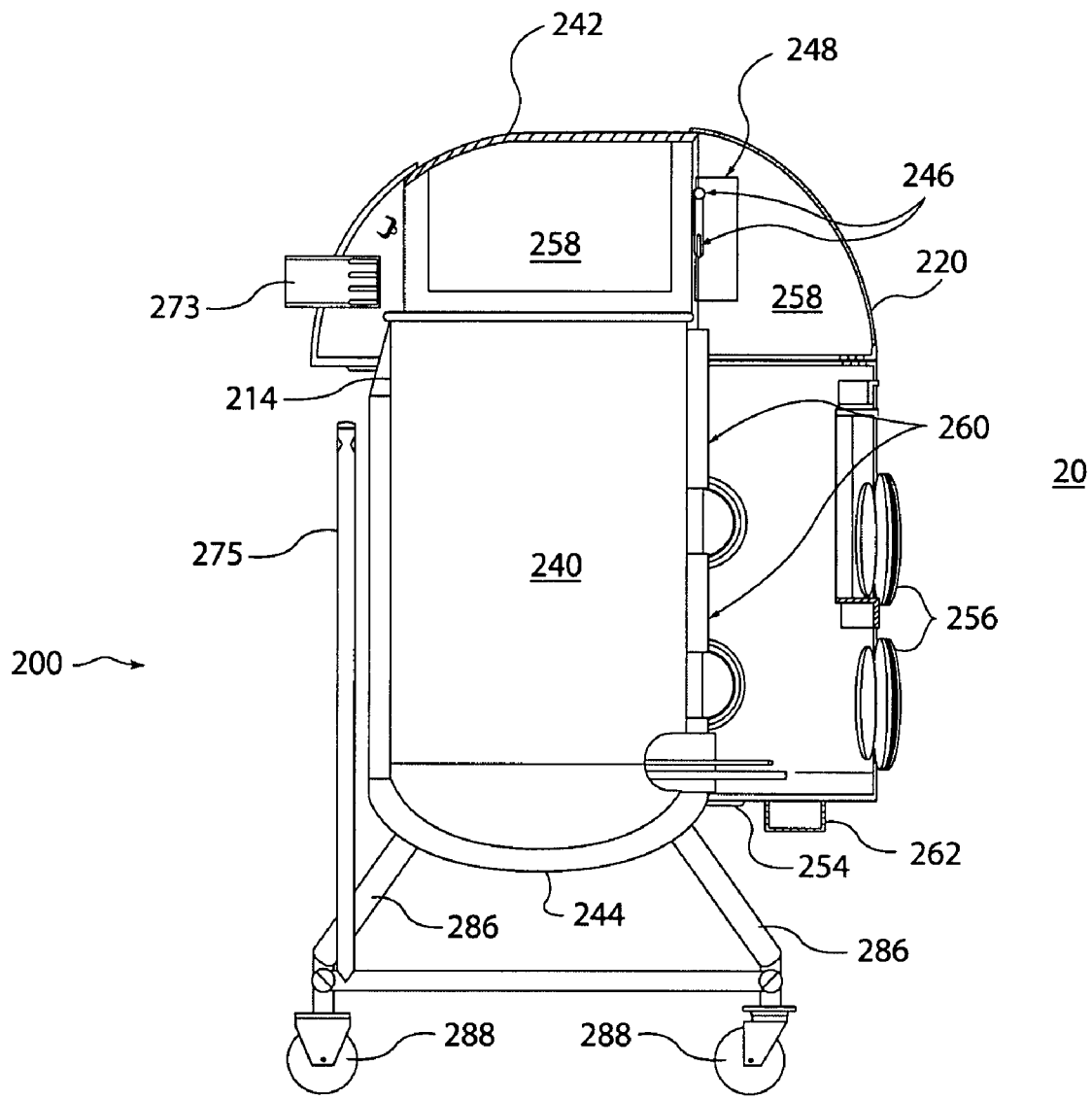
FIG. 5 is a schematic diagram showing a side view of a bioreactor provided with an environmental containment enclosure, according to an embodiment of the invention.
Figure 6:
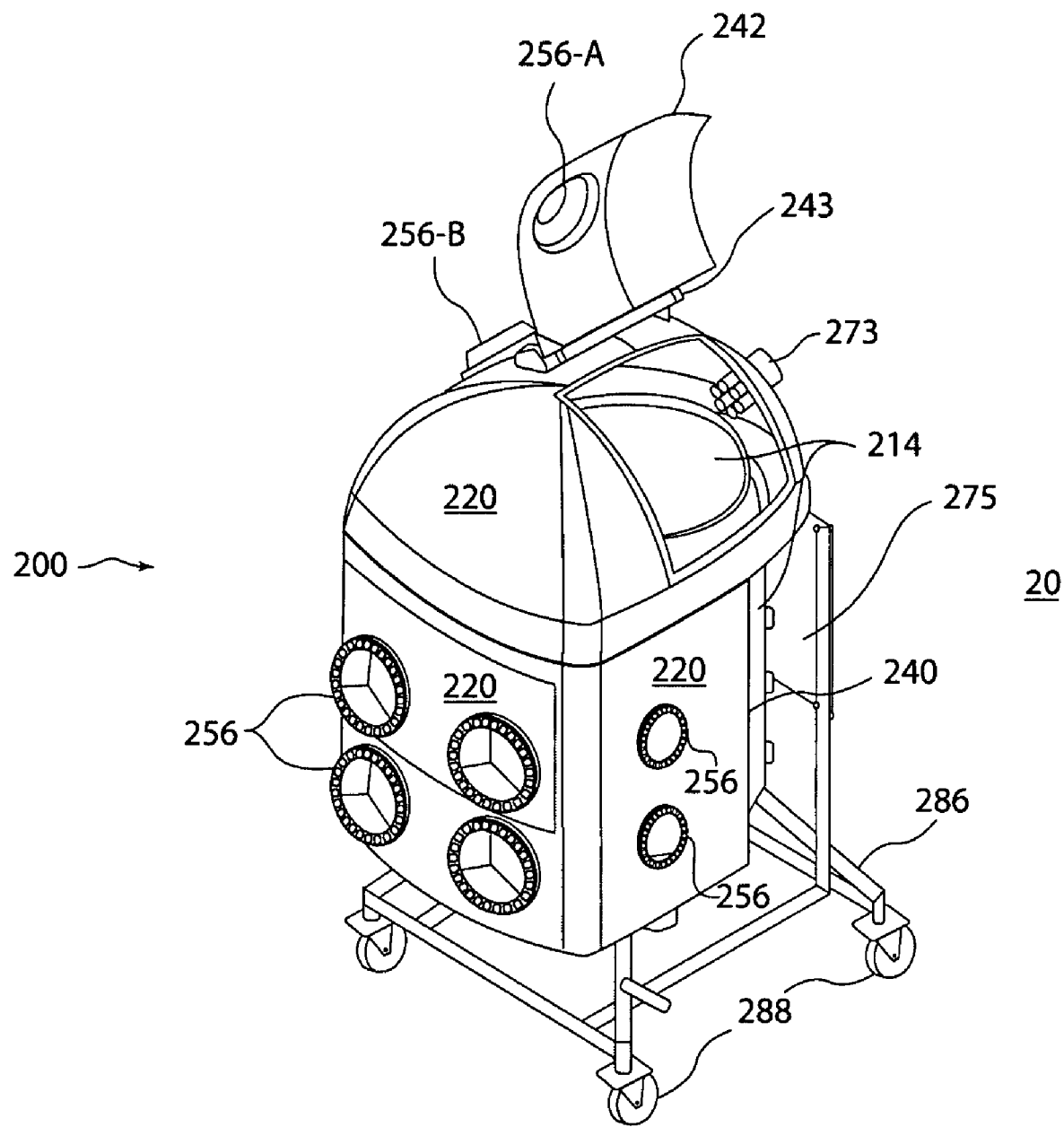
FIG. 6 is a schematic diagram showing a perspective view of the bioreactor provided with an environmental containment enclosure of FIG. 5, according to an embodiment of the invention.
Figure 7:
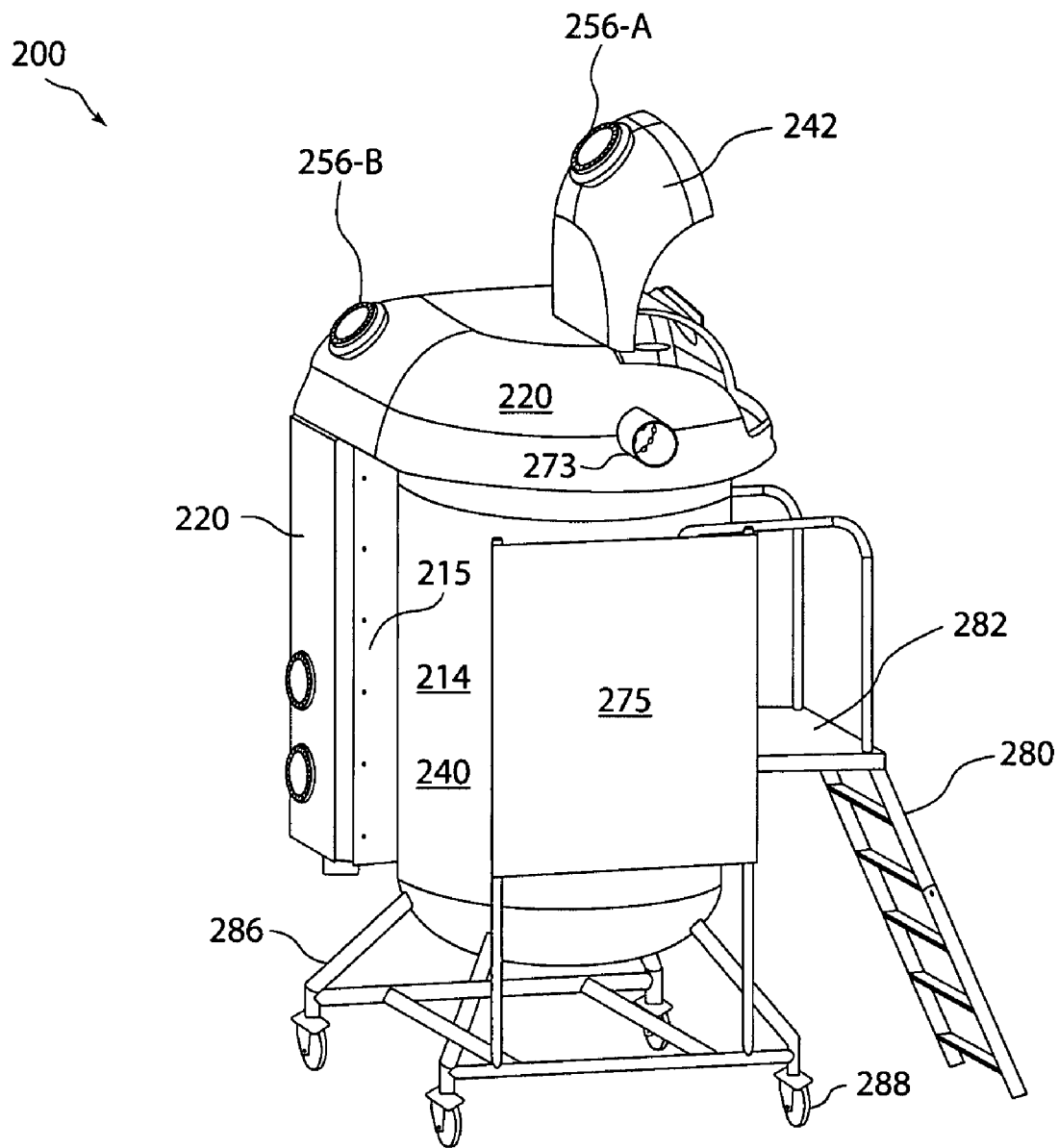
FIG. 7 is a schematic diagram showing another perspective view of the bioreactor provided with an environmental containment enclosure of FIG. 5, according to an embodiment of the invention.

Additional examples of apparatuses having environmental containment are shown in the embodiments illustrated in FIGS. 5-7. FIG. 5 shows a side view of an apparatus having environmental containment according to one embodiment of the invention. Apparatus 200 includes a vessel 214 (e.g., a support structure containing a collapsible bag container) and an environmental containment enclosure 220, which surrounds a top portion and some side portions of the vessel. As shown, bottom portion 244 may be exposed to atmosphere 20. Environmental containment enclosure 220 also includes a door 242 allowing access to a top portion of the vessel. The door can be closed to provide an air tight seal between an enclosed space 258 and atmosphere 20. Rods 246 may be attached to the environmental containment enclosure 220 and may extend over a top portion of vessel 214. The rods can support various components that may be operatively associated with the vessel, such as a motor (e.g., for rotating an impeller). The apparatus may optionally include one or more filters 248, which may be in fluid communication with an outlet (e.g., an exhaust port) of the vessel and/or of a collapsible bag contained in the vessel. The outlet can allow gases, after being filtered by one or more filters 248, to exit the vessel or collapsible bag into the atmosphere or into enclosed space 258 within environmental containment enclosure 220.

As shown in this illustrative embodiment, environmental containment enclosure 220 also includes access ports 256, here shown in the form of iris ports, that allow a user access to enclosed space 258. A user can use enclosed space 258 as a working space for accessing material within vessel 214. Material can be accessed in the vessel via a sampling port 254, which may be embedded and/or irreversibly/reversibly attached to the vessel in some embodiments. Thus, a user positioned outside of the enclosure 220 can access a material within the vessel 214 via the ports without subjecting the material to an atmosphere 20 surrounding the environmental containment enclosure. The environmental containment enclosure 220 can prevent or decrease the amount of contamination, e.g., from personnel, equipment, and ambient air, of a material contained in the vessel 214 and/or the degree of exposure of a user to the material. Any tools or components that may be used for sampling or other purposes may be left inside the enclosed space 258 in a box 262 built into the environmental containment enclosure 220. Clear panels 260 allow the user visual access into vessel 214. The environmental containment enclosure 220 may also be formed of a transparent material to allow visual access.

Also shown in FIG. 5, the apparatus includes a filter 273 (e.g., a HEPA filter) associated with environmental containment enclosure 220. Filter 273 may be used to filter or condition the gases (e.g., air) entering and/or exiting the environmental containment enclosure. Optionally, filter 273 is associated with one or more of a fan, compressor, blower, damper control, pressurized gas cylinder, and/or other source of gas.

Figure 8:
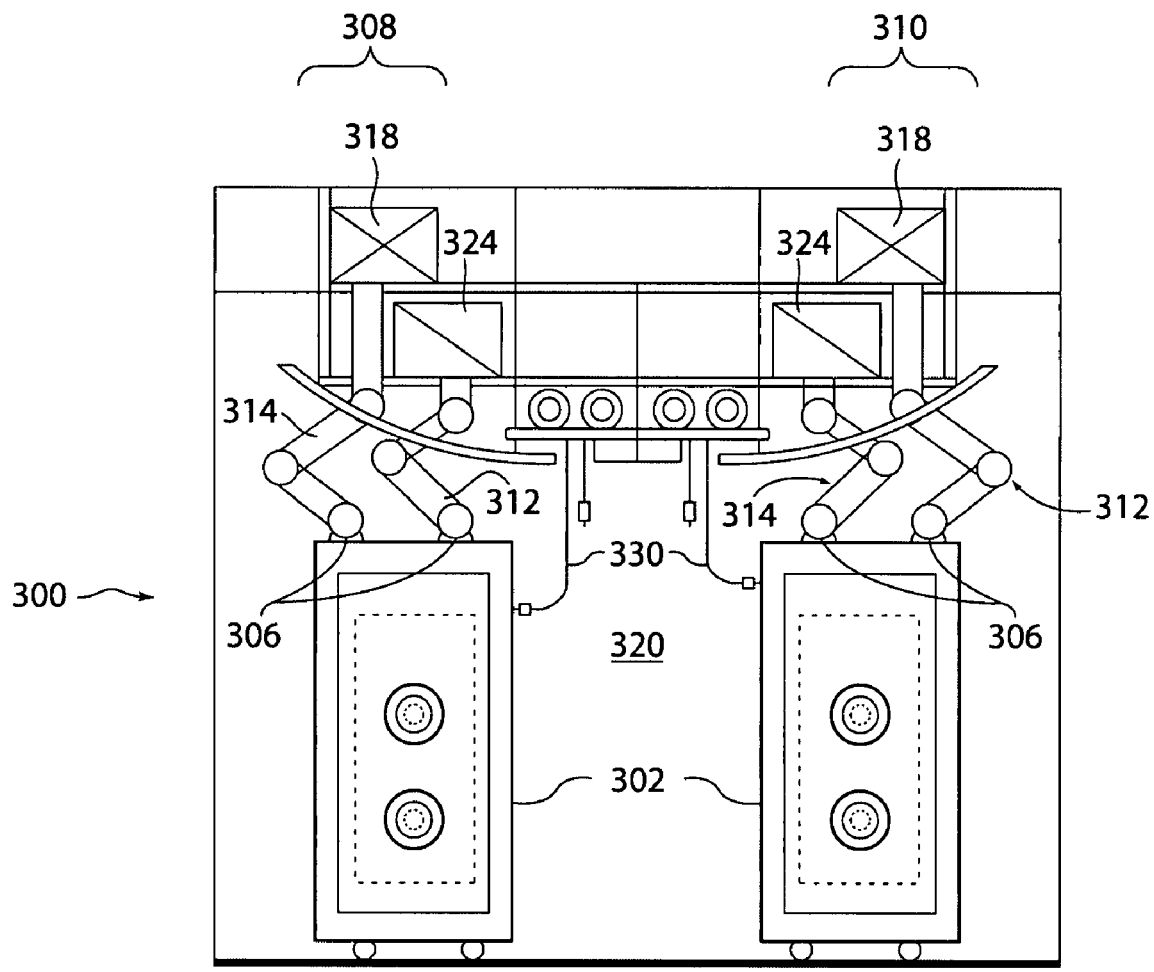
FIG. 8 is a schematic diagram showing a side view of two environmental containment enclosures interconnected with a ventilation system, according to an embodiment of the invention.
Figure 9:
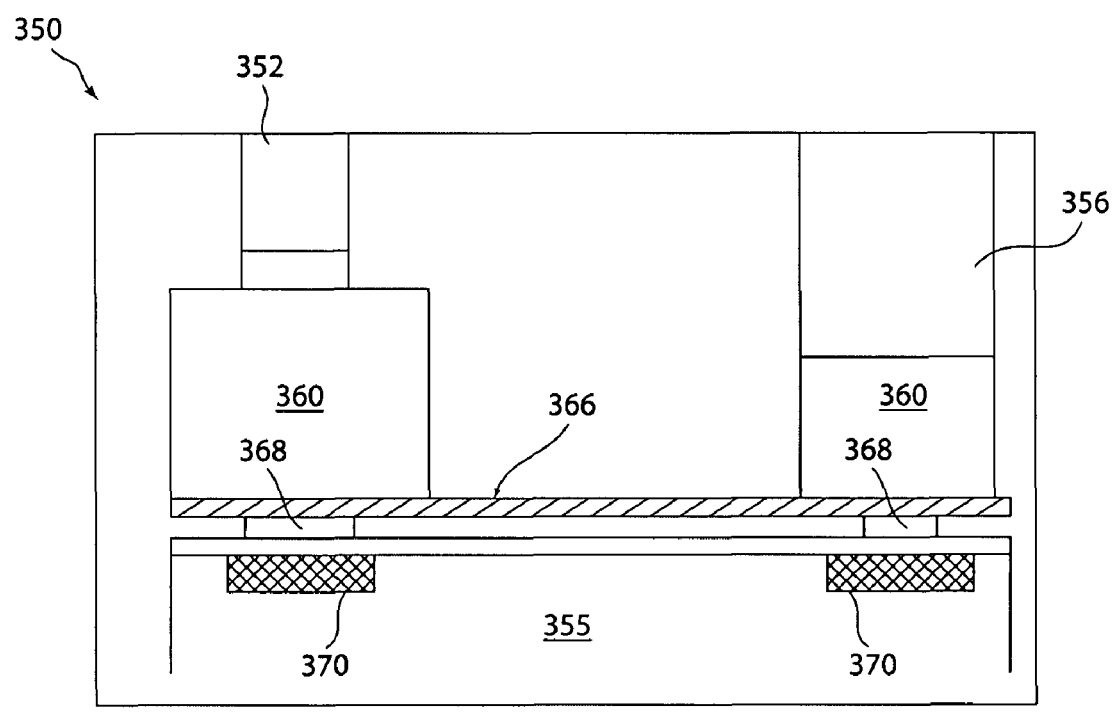
FIG. 9 is a schematic diagram showing an individual ventilation system associated with an environmental containment enclosure, according to an embodiment of the invention.

In one embodiment, apparatus 200 is connected with one or more other apparatuses to a common ventilation system (e.g., as illustrated in FIG. 8 described in more detail below). In another embodiment, apparatus 200 includes its own ventilation system, which may be attached to mounting panel 275, for example. An example of such a ventilation system is illustrated in FIG. 9 below. In yet other embodiments, a ventilation system may be positioned entirely within an environmental containment enclosure.

Although not shown, apparatus 200 may include, in some embodiments, one or more connection ports for interconnecting an interior of the vessel to an interior of a second apparatus. Additionally or alternatively, the apparatus may include one or more connection ports adapted for connecting an interior of environmental containment enclosure 220 to an interior of a second environmental containment enclosure of another apparatus. Of course, apparatus 200 may include any suitable number of inlet and outlet ports for introducing and/or removing gases and/or liquids to/from the apparatus.

The apparatus may further include a plurality of supports 286, optionally with wheels 288 for facilitating transport of the apparatus.

It should be understood that not all of the features shown in FIG. 5 need be present in all embodiments of the invention and that the illustrated elements may be otherwise positioned or configured. Also, in other embodiments, additional elements may be present in apparatus 200 such as elements described herein.

FIG. 6 shows a perspective view of apparatus 200 according to an embodiment of the invention. As shown in this illustrative embodiment, environmental containment enclosure 220 includes a door 242 associated with a hinge 243 and having an access port 256-A. The access port allows a user access into a top portion of an enclosed space formed by the environmental containment enclosure when the door is closed. An access port 256-B may optionally be present at another top portion of the environmental containment enclosure.

FIG. 7 shows another perspective view of apparatus 200 according to an embodiment of the invention. As shown in this illustrative embodiment, vessel 214 includes a flange 215 protruding from a side portion 240 of the vessel. Environmental containment enclosure 220 can be reversibly or irreversibly attached to the flange to form an air-tight seal with the vessel. Attachment may occur, for example, by welding (e.g., heat welding and ultrasonic welding), bolting, use of adhesives, fastening, latching, clamping, or other attaching techniques. Also shown is a ladder 280 and a support 282, each of which may be reversibly or irreversibly attached to mounting panel 275 and/or vessel 214. The ladder and support may be provided for large vessels to allow a user access to a top portion of the vessel and/or enclosure.

As mentioned, in some embodiments, an apparatus of the invention includes or is connected with a ventilation system that can help maintain an aseptic, sterile, substantially particle-free, or reduced particulate concentration environment within a containment apparatus (e.g., a vessel and/or an environmental containment enclosure). One example of an external ventilation system is shown in the embodiment illustrated in FIG. 8. System 300 includes apparatuses 302 having environmental containment enclosures and including ports 306 that are dimensioned for connection to ventilation systems 308 and 310 via tubes 312 and 314, respectively. Tubes 312 extend from sources of gas 318 and tubes 314 extend from exhaust systems 324 to the apparatuses. As shown in the illustrative embodiment, the tubes may be flexible, which can facilitate connection to each apparatus so as not to restrict a location of an apparatus in working space 320. Additionally, electrical and/or data connections 330 may be made to each apparatus.

The gas supplied to the apparatuses may be delivered from source of gas 318 (e.g. a fan, compressor, blower, or pressurized gas cylinder) through a gas handler (not shown) that controls temperature (e.g., 15-30 degrees C.) or relative humidity (e.g., 10-60% RH). The pressure within the enclosed spaces of the apparatuses can also be controlled using the gas handler. The gas may delivered via tube 314 to an apparatus intake blower (not shown), where the gas may be pre-filtered and even HEPA filtered prior to entry into the apparatus.

In some embodiments, apparatuses described herein include an individual ventilation system associated with or contained at least partially or completely within each of the apparatuses. Thus, apparatuses that are mobile and include an individual ventilation system associated therewith are not restricted in movement by being connected to a fixed position ventilation system, such as the ones shown in FIG. 8. An example of an individual ventilation system associated with an apparatus is shown in FIG. 9. As shown in this exemplary embodiment, a ventilation system 350 includes a source of gas unit 352 for introducing gas into apparatus 355 and an exhaust unit 356 for removing a gas from the apparatus. Each unit may include separate fans, controls, and duct work. In addition, each unit may include a designated filtration system 360 (e.g., a HEPA filtration system). A damper control associated with one or both of the units may be used to regulate pressurization within an apparatus during processing. For example, using a source of gas unit rated at 700 cubic feet per minute, the system may maintain 0.1-0.3 inches water column positive pressure within the apparatus. In other embodiments, a source of vacuum may be associated with one of the units for producing a pressure which is less than atmospheric pressure inside an enclosure of the apparatus.

Units 352 and 356 and any associated filtration systems may be attached to a support frame 366. Fluid communication between the units and apparatus 355 may occur via ports 368. Optionally, apparatus 355 may include filters 370 for preventing materials (e.g., liquids, particles, or organisms) from entering and/or exiting the apparatus.

It should be understood that the ventilation systems shown in connection with FIGS. 8 and 9 are exemplary and that in other embodiments, ventilation systems having other configurations can be associated with apparatuses described herein.

Various embodiments described herein include a container such as a collapsible bag. "Flexible container", "flexible bag", or "collapsible bag" as used herein, indicates that the container or bag is unable to maintain its shape and/or structural integrity when subjected to the internal pressures (e.g., due to the weight and/or hydrostatic pressure of liquids and/or gases contained therein expected during operation) without the benefit of a separate support structure. The collapsible bag may be made out of inherently flexible materials, such as many plastics, or may be made out of what are normally considered rigid materials (e.g., glass or certain metals) but having a thickness and/or physical properties rendering the container as a whole unable to maintain its shape and/or structural integrity when subjected to the internal pressures expected during operation without the benefit of a separate support structure. In some embodiments, collapsible bags include a combination of flexible and rigid materials; for example, the bag may include rigid components such as connections, ports, supports for a mixing and/or antifoaming system, etc.

The container (e.g., collapsible bag) may have any suitable size for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible.

In some embodiments, the collapsible bag is disposable and is formed of a suitable flexible material. The flexible material may be one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. As noted above, portions of the flexible container may comprise a substantially rigid material such as a rigid polymer (e.g., high density polyethylene), metal, and/or glass (e.g., in areas for supporting fittings, etc.). In other embodiments, the container is made of a substantially rigid material. All or portions of the container may be optically transparent to allow viewing of contents inside the container. The materials or combination of materials used to form the container may be chosen based on one or more properties such as flexibility, puncture strength, tensile strength, liquid and gas permeabilities, opacity, and adaptability to certain processes such as blow molding, injection molding, or spin cast molding (e.g., for forming seamless collapsible bags).

The container (e.g., collapsible bag) may have any suitable thickness for holding a liquid and may be designed to have a certain resistance to puncturing during operation or while being handled. For instance, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In some embodiments, the container includes more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container. It should be understood that a container may be formed of any suitable combinations of layers. The container (e.g., collapsible bag) may include, for example, 1 layer, greater than or equal to 2 layers, greater than or equal to 3 layers, or greater than or equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In one set of embodiments of the invention, the container is seamless. The container may be, for example, a seamless collapsible bag or a seamless rigid (or semi-rigid) container. Many existing collapsible bags are constructed from two sheets of a plastic material joined by thermal or chemical bonding to form a container having two longitudinal seams. The open ends of the sheets are then sealed using known techniques and access apertures are formed through the container wall. During use, collapsible bags having seams can cause the formation of crevices at or near the seams where fluids or reagents contained therein are not thoroughly mixed. In certain embodiments involving, for example, the use of collapsible bags for performing a chemical, biochemical and/or biological reaction, unmixed reagents can cause a reduction in yield of a desired product. The presence of seams in a collapsible bag can also result in the inability of the collapsible bag to conform to the shape of a reusable support structure that may support the bag. By using collapsible bags without any seams joining two or more flexible wall portions of the bag, however, the problems of mixing and conformity may be avoided or reduced. In certain embodiments, seamless collapsible bags can be made specifically to fit a particular reusable support structure having a unique shape and configuration. Substantially perfect-fitting collapsible bags can be used, for example, as part of a bioreactor system or a biochemical and/or chemical reaction system. Seamless rigid or semi-rigid containers may also be beneficial in some instances.

In one embodiment, a seamless collapsible bag is formed in a process in which the bag liner (e.g., the flexible wall portions of the bag), as well as one or more components such as a component of an agitator/mixer system (e.g., a shaft and/or a support base), port, etc. is cast from one continuous supply of a polymeric precursor material. In some cases, the casting may occur without hermetically sealing, e.g., via welding. Such a seamless collapsible bag may allow the interior liquid or other product to contact a generally even surface, e.g., one which does not contain substantial wrinkles, folds, crevices, or the like. In addition, in some cases, the collapsible bag complementarily fits within a support structure when installed and filled with a liquid or product. The seamless collapsible bag may also have a generally uniform polymeric surface chemistry which may, for example, minimize side reactions. Methods of forming seamless collapsible bags involving more than one polymeric precursor materials can also be performed.

Seamless collapsible bags can be created by a variety of methods. In one embodiment, a seamless collapsible bag is formed by injecting liquid plastic into a mold that has been pre-fitted with components such as ports, connections, supports, and rigid portions configured to support a mixing system (e.g., a shaft and/or a base) that are subsequently surrounded, submerged, and/or embedded by the liquid plastic. The component may be a rigid component, e.g., one that can substantially maintain its shape and/or structural integrity during use. Any suitable number of components (e.g., at least 1, 2, 5, 10, 15, etc.) can be integrated with containers (e.g., collapsible bags) using methods described herein. The mold may be designed to form a collapsible bag having the shape and volume of the mold, which may have a substantially similar shape, volume, and/or configuration of a reusable support structure.

In one embodiment, the container is formed by using an embedded component/linear molding (ECM) technique. In one such technique, rigid or pre-made components such as tube ports, agitator bases, etc. are first positioned in the mold. A polymer or polymer precursor used to form a container (e.g., a seamless collapsible bag) may be introduced (e.g., in a melt state) via a polymer fabrication technique such as those described below. In some cases, a component or a portion of the component is partially melted by the polymer precursor, allowing the component to form a continuous element with the container. That is, the component can be joined (e.g., fused) with one or more wall portions of the container (e.g., flexible wall portions of a collapsible bag) to form a single, integral piece of material without seams.

In certain embodiments, especially in curtain embodiments involving fluid manipulations or carrying out a chemical, biochemical and/or biological reaction in a vessel, the vessel is substantially closed, e.g., the vessel is substantially sealed from the environment outside of the container except, in certain embodiments, for one or more inlet and/or outlet ports that allow addition to, and/or withdrawal of contents from, the vessel. If a collapsible bag is used, it may be substantially deflated prior to being filled with a liquid, and may begin to inflate as it is filled with liquid. In other embodiments, aspects of the invention can be applied to opened vessel systems.

In some cases, fluids may be introduced and/or removed from a vessel, container, or unit operation component via inlet ports and/or outlet ports. The vessel may be a part of a reactor system for performing a biological, biochemical, or chemical reaction, or may be in the form of a unit operation component such as a filtration system, seed culture expansion system, primary recovery system, chromatography system, filling system, closed media/buffer preparation system, and water purification system, for example. The vessel may have any suitable number of inlet ports and any suitable number of outlet ports. In some cases, pumps, such as disposable pumps, may be used to introduce a gas or other fluid into the vessel, e.g., via an inlet port, and/or which may be used to remove a gas or other fluid from the vessel, e.g., via an outlet port.

In certain embodiments, a vessel may be in the form of a support structure, for example, vessel 114 as shown in FIG. 4, which can surround and contain container 118. The support structure may have any suitable shape able to surround and/or contain the container. In some cases, the support structure is reusable. The support structure may be formed of a substantially rigid material. Non-limiting examples of materials that can be used to form the reusable support structure include stainless steel, aluminum, glass, resin-impregnated fiberglass or carbon fiber, polymers (e.g., high-density polyethylene, polyacrylate, polycarbonate, polystyrene, nylon or other polyamides, polyesters, phenolic polymers, and combinations thereof. The materials may be certified for use in the environment in which it is used. For example, non-shedding materials may be used in environments where minimal particulate generation is required.

In some embodiments, the reusable support structure may be designed to have a height and diameter similar to standard industrial size stainless steel bioreactors (or other standard reactors or vessels). The design may also be scaleable down to small volume bench reactor systems. Accordingly, the reusable support structure may have any suitable volume for carrying out a desired chemical, biochemical and/or biological reaction. In many instances, the reusable support structure has a volume substantially similar to that of the container. For instance, a single reusable support structure may be used to support and contain and single container having a substantially similar volume. In other cases, however, a reusable support structure is used to contain more than one container. The reusable support structure may have a volume between, for example, 1-100 L, 100-200 L, 200-300 L, 300-500 L, 500-750 L, 750-1,000 L, 1,000-2,000 L, 2,000-5,000 L, or 5,000-10,000 L. In some instances, the reusable support structure has a volume greater than 1 L, or in other instances, greater than 10 L, 20 L, 40 L, 100 L, 200 L, 500 L, or 1,000 L. Volumes greater than 10,000 L are also possible.

In other embodiments, however, a vessel of the present invention does not include a separate container (e.g., collapsible bag) and support structure, but instead comprises a self-supporting disposable or reusable container. The container may be, for example, a plastic vessel and, in some cases, may include an agitation system integrally or removably attached thereto. The agitation system may be disposable along with the container. In one particular embodiment, such a system includes an impeller welded or bolted to a polymeric container. It should therefore be understood that many of the aspects and features of the vessels described herein with reference to a container and a support structure (for example, a seamless container, a sparging system, an antifoaming device, etc.), are also applicable to a self-supporting disposable container.

Furthermore, a vessel may include various sensors and/or probes for controlling and/or monitoring one or more process parameters inside the vessel such as, for example, temperature, pressure, pH, dissolved oxygen (DO), dissolved carbon dioxide ($DCO_2$), mixing rate, and gas flow rate. The sensor may also be an optical sensor in some cases.

In some embodiments, process control may be achieved in ways which do not compromise the sterile barrier established by a vessel, container, or environmental containment enclosure. For example, gas flow may be monitored and/or controlled by a rotameter or a mass flow meter upstream of an inlet air filter. In another embodiment, disposable optical probes may be designed to use "patches" of material containing an indicator dye which can be mounted on the inner surface of the disposable container and read through the wall of the disposable container via a window in the reusable support structure. For example, dissolved oxygen, pH, and/or $CO_2$ each may be monitored and controlled by an optical patch and sensor mounted on, e.g., a gamma-irradiatable, biocompatible polymer which, can be sealed to, embedded in, or otherwise attached to the surface of the container.

A vessel may be operatively associated with a temperature controller which may be, for example, a heat exchanger, a closed loop water jacket, an electric heating blanket, or a Peltier heater. Other heaters for heating a liquid inside a vessel are known to those of ordinary skill in the art and can also be used in combination with apparatuses described herein. The heater may also include a thermocouple and/or a resistance temperature detector (RTD) for sensing a temperature of the contents inside the vessel. The thermocouple may be operatively connected to the temperature controller to control temperature of the contents in the vessel. Optionally, a heat-conducting material may be embedded in the surface of the vessel to provide a heat transfer surface to overcome the insulating effect of the material used to form other portions of the vessel.

Cooling may also be provided by a closed loop water jacket cooling system, a cooling system mounted on the reactor, or by standard heat exchange through a cover/jacket on the reusable support structure (e.g., the heat blanket or a packaged dual unit which provides heating and cooling may a component of a device configured for both heating/cooling but may also be separate from a cooling jacket). Cooling may also be provided by Peltier coolers. For example, a Peltier cooler may be applied to an exhaust line to condense gas in the exhaust air to help prevent an exhaust filter from wetting out.

In certain embodiments, an apparatus includes gas cooling for cooling the head space and/or exit exhaust. For example, jacket cooling, electrothermal and/or chemical cooling, or a heat exchanger may be provided at an exit air line and/or in the head space of a container. This cooling can enhance condensate return to the container, which can reduce exit air filter plugging and fouling. In some embodiments, purging of pre-cooled gas into the head space can lower the dew point and/or reduce water vapor burden of the exit air gas.

In some cases, sensors and/or probes may be connected to a sensor electronics module, the output of which can be sent to a terminal board and/or a relay box. The results of the sensing operations may be input into a computer-implemented control system (e.g., a computer) for calculation and control of various parameters (e.g., temperature and weight/volume measurements) and for display and user interface. Such a control system may also include a combination of electronic, mechanical, and/or pneumatic systems to control heat, air, and/or liquid delivered to or withdrawn from the disposable container as required to stabilize or control the environmental parameters of the process operation. It should be appreciated that the control system may perform other functions and the invention is not limited to having any particular function or set of functions.

The one or more control systems described herein can be implemented in numerous ways, such as with dedicated hardware and/or firmware, using a processor that is programmed using microcode or software to perform the functions recited above or any suitable combination of the foregoing. A control system may control one or more operations of a single reactor for a biological, biochemical or chemical reaction, or of multiple (separate or interconnected) reactors.

Each of systems described herein, and components thereof, may be implemented using any of a variety of technologies, including software (e.g., C, C#, C++, Java, or a combination thereof), hardware (e.g., one or more application-specific integrated circuits), firmware (e.g., electrically-programmed memory) or any combination thereof.

Various embodiments according to the invention may be implemented on one or more computer systems. These computer systems, may be, for example, general-purpose computers such as those based on Intel PENTIUM-type and XScale-type processors, Motorola PowerPC, Motorola DragonBall, IBM HPC, Sun UltraSPARC, Hewlett-Packard PA-RISC processors, any of a variety of processors available from Advanced Micro Devices (AMD) or any other type of processor. It should be appreciated that one or more of any type of computer system may be used to implement various embodiments of the invention. The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

In one embodiment, a control system operatively associated with an apparatus or vessel described herein is portable. The control system may include, for example, all or many of the necessary controls and functions required to perform a fluidic manipulation (e.g., mixing and reactions) in the control system. The control system may include a support and wheels for facilitating transport of the vessel. Advantageously, such a portable control system can be programmed with set instructions, if desired, transported (optionally with the vessel), and hooked up to a vessel, ready to perform a fluid manipulation in a shorter amount of time than conventional fluid manipulation control systems (e.g., less than 1 week, 3 days, 1 day, 12 hours, 6 hours, 3 hours, or even less than 1 hour).

An apparatus, including a vessel, may also be connected to one or more sources of gases such as air, oxygen, carbon dioxide, nitrogen, ammonia, or mixtures thereof. The gases may be compressed, pumped, etc. Such gases may be used to provide suitable growth and/or reaction conditions for producing a product inside the vessel. The gases may also be used to provide sparging to the contents inside the vessel, e.g., for mixing or other purposes. For instance, in certain embodiments employing spargers, bubble size and distribution can be controlled by passing an inlet gas stream through a porous surface prior to being added to the vessel. Additionally, the sparging surface may be used as a cell separation device by alternating pressurization and depressurization (or application of vacuum) on the exterior surface of the porous surface, or by any other suitable method.

In one embodiment, a vessel or container is connected to various sources of gases and the inlet gases may optionally pass through a filter, a flow meter, and/or a valve, which may be controlled by controller system, prior to entering the vessel or container. The valve may be a pneumatic actuator (actuated by, e.g., compressed air/carbon dioxide or other gas), which may be controlled by a solenoid valve. These solenoid valves may be controlled by a relay connected to terminal board, which is connected to the controller system. The terminal board may comprise, for example, a PCI terminal board, or a USB/parallel, or fire port terminal board of connection. In other embodiments, flush closing valves can be used for addition ports, harvest and sampling valves. Progressive tubing pinch valves that are able to meter flow accurately can also be used. In some cases, the valves may be flush closing valves (e.g., for inlet ports, outlet ports, sampling ports, etc.). The inlet gases may be connected to any suitable inlet of the vessel or container. In one embodiment, the inlet gases are associated with one or more spargers which can be controlled independently, as described in more detail below.

As shown in the exemplary embodiment illustrated in FIG. 4, a vessel comprising a container can be operatively associated with a variety of components as part of an overall apparatus 100, according to another aspect of the invention. Accordingly, the container and/or support structure may include several fittings to facilitate connection to functional component such as filters, sensors, and mixers, as well as connections to lines for providing reagents such as liquid media, gases, and the like. The container and the fittings may be sterilized prior to use so as to provide a "sterile envelope" protecting the contents inside the container from airborne contaminants outside. In some embodiments, the contents inside the container do not contact the reusable support structure and, therefore, the reusable support structure can be reused after carrying out a particular chemical, biochemical and/or biological reaction without being sterilized, while the container and/or fittings connected to the container can be discarded. In other embodiments, the container, fittings, and/or reusable support structure may be reused (e.g., after cleaning and sterilization).

A vessel may also include, in some embodiments, a mixing system for mixing contents of a container and/or an antifoaming system for removing or reducing foam in a headspace of the container. The mixing and/or antifoaming system may include an agitator or mixer. In some cases, more than one agitator or mixer may be used, and the agitators and/or mixers may the same or different. More than one agitation system may be used, for example, to increase mixing power. In some cases, the agitator may be one in which the height can be adjusted, e.g., such that the draft shaft allows raising of an impeller or agitator above the bottom of the tank and/or allows for multiple impellers or agitators to be used. A mixing system of a vessel may be disposable or intended for a single use (e.g., along with the container), in some cases.

Various methods for mixing fluids can be implemented in a container. For instance, mixers based on magnetic actuation, sparging, and/or air-lift can be used. Direct shaft-drive mixers that are sealed and not magnetically coupled can also be used. In one particular embodiment, mixing systems such as the ones disclosed in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, and a PCT Application entitled, "Gas Delivery Configurations, Foam Control Systems, and Bag Molding Methods and Articles for Collapsible Bag Vessels," filed on Jun. 15, 2007, each of which is incorporated herein by reference in its entirety, are used with embodiments described herein. For example, the mixing system may include a motor, e.g., for driving an impeller (or other component used for mixing) positioned inside the container, a power conditioner, and/or a motor controller.

In some cases, a plurality (e.g., more than 1, 2, or 3, etc.) of mixers or impellers are used for mixing contents in a container. Additionally or alternatively, a mixing system may include an adjustable height impeller and/or an impeller with varying impeller blade configurations. For instance, the mixer may have an extended drive shaft which allows the impeller to be raised to different heights relative to the bottom of the container. The extended shaft can also allow integration of multiple impellers. In another embodiment, a bioreactor system includes more than one agitation drive per container, which can increase mixing power.

To enhance mixing efficiency, the container may include baffles such as internal film webs or protrusions, e.g., positioned across the inside of the container or extending from the inner surface of the container at different heights and at various angles. The baffles may be formed of in any suitable material such as a polymer, a metal, or a ceramic so long as they can be integrated with the container.

In one embodiment, a direct drive agitator is used. Typically, the agitator includes a direct shaft drive that is inserted into the container. In certain instances, the location where the shaft exits the container may be maintained in a sterile condition. For instance, internal and/or external rotating seals may be used to maintain a sterile seal, and/or live hot steam may be used to facilitate maintenance of the sterile seal. By maintaining such a sterile seal, contamination caused by the shaft, e.g., from the external environment, from the exiting gases, etc., may be reduced or avoided.

In another embodiment, a magnetic agitator is used. Typically, a magnetic agitator uses magnets such as fixed or permanent magnets to rotate or otherwise move the agitator, for example, impellers, blades, vanes, plates, cones, etc. In some cases, the magnets within the magnetic agitator are stationary and can be turned on or activated in sequence to accelerate or decelerate the agitator, e.g., via an inner magnetic impeller hub. As there is no penetration of the container by a shaft, there may be no need to maintain the agitator in a sterile condition, e.g., using internal and/or external rotating seals, live hot steam, or the like.

In yet another embodiment, an electromechanical polymeric agitator is used, e.g., an agitator that includes an electromechanical polymer-based impeller that spins itself by "paddling," i.e., where the agitator is mechanically flapped to propel the agitator or impeller, e.g., rotationally.

Specific non-limiting examples of devices that can be used as a mixing system, and/or an antifoaming system in certain embodiments, are illustrated in FIGS. 10A-12. The devices shown include a magnetically-actuated impeller, although other arrangements are possible. In some of these magnetic configurations, the motor is not directly connected to the impeller. Magnets associated with a drive head can be aligned with magnets associated with an impeller hub, such that the drive head can rotate the impeller through magnetic interactions. In some cases, the motor portion (and other motor associated components) may be mounted on the support structure.

Figure 10A:
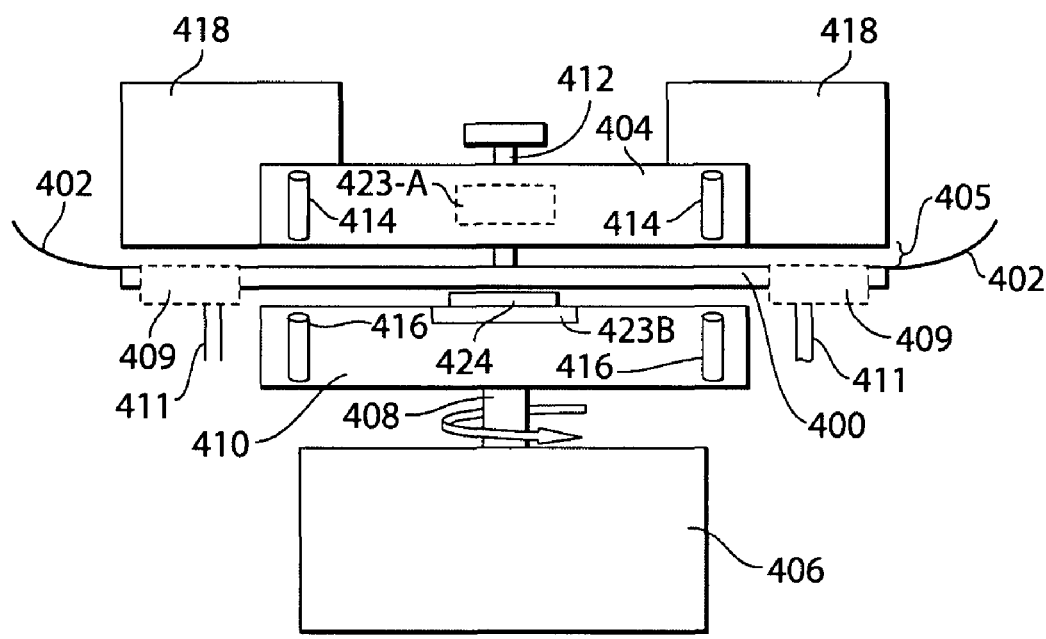
FIGS. 10A-10B illustrate various impeller-comprising mixing devices, according to an embodiment of the invention.

As shown in the embodiment illustrated in FIG. 10A, this exemplary system generally includes an impeller support 400 affixed to portions of a container wall 402 (e.g., a collapsible bag) at a lower portion thereof, an impeller hub 404, a motor 406, a motor shaft 408 and a drive head 410. The impeller support may be affixed to the wall of the container using any suitable technique, e.g., by heat welding together two portions of a two-piece impeller support, sandwiching the container wall therebetween or onto the wall, or using other methods described herein. As one example, an opening in the wall of the container may be used to allow a central portion of the impeller plate to extend from an exterior of the container to the interior (or vise versa). Then a sealing ring (not shown) may be adhered or the container may be welded directly to an outer circumference of the impeller support to seal the container wall therebetween. As another example, an undersized opening in the wall of the container may be used to form a seal with a circumferencial edge of the impeller support slightly larger than the opening. In other embodiments, at least a portion of the impeller support is embedded with a wall of the container and/or the impeller support and container are fabricated simultaneously (e.g., by spin casting, injection molding, or blow molding).

In some embodiments, one or more spargers is associated with an impeller support, which may be used to direct air or other gases into the container. In some cases, the sparger may include porous, micro-porous, or ultrafiltration elements 409 (e.g., sparging elements). The spargers may be used to allow a gaseous sparge or fluids into and/or out of the container by being dimensioned for connection to a source of a gas; this connection may take place via tubing 411. Such sparging and/or fluid addition or removal may be used, in some cases, in conjunction with a mixing system (e.g., the rotation of the impeller hub). Sparging systems are described in more detail below.

In the embodiment illustrated in FIG. 10A, the interior side of the impeller support may include a shaft or post 412 to which a central opening in the impeller hub 404 receives. The impeller hub may be maintained at a slight distance 405 above the surface of the impeller support (e.g., using a physical spacer) to prevent friction therebetween. Low friction materials may be used in the manufacture of the impeller hub to minimize friction between the impeller hub and the post. In another embodiment, one or more bearings may be included to reduce friction. For instance, the impeller hub may include, in certain instances, a bearing 423-A (e.g., a roller bearing, ball bearing (e.g., a radial axis ball bearing), thrust bearing, race bearing; double raceway bearing, lazy-susan bearing, or any other suitable bearing) for reducing or preventing friction between the impeller support and the post. Additionally, the drive head may include a bearing 423-B, the same as or different from bearing 423-A, and/or a physical spacer 424 for reducing or preventing friction between the drive head and the impeller support.

The impeller hub also may include one or more magnets 414, which may be positioned at a periphery of the hub or any other suitable position, and may correspond to a position of a magnet(s) 416 provided on the drive head 410. The poles of the magnets may be aligned in a manner that increases the amount of magnetic attraction between the magnets of the impeller hub and those of the drive head.

The drive head 410 may be centrally mounted on a shaft 408 of motor 406. The impeller hub also may include one or more impeller blades 418. In some cases, the embedded magnet(s) in the impeller can also be used to remove ferrous or magnetic particles from solutions, slurries, or powders.

Further examples of mixing systems are described in more detail in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, which is incorporated herein by reference.

Figure 10B:
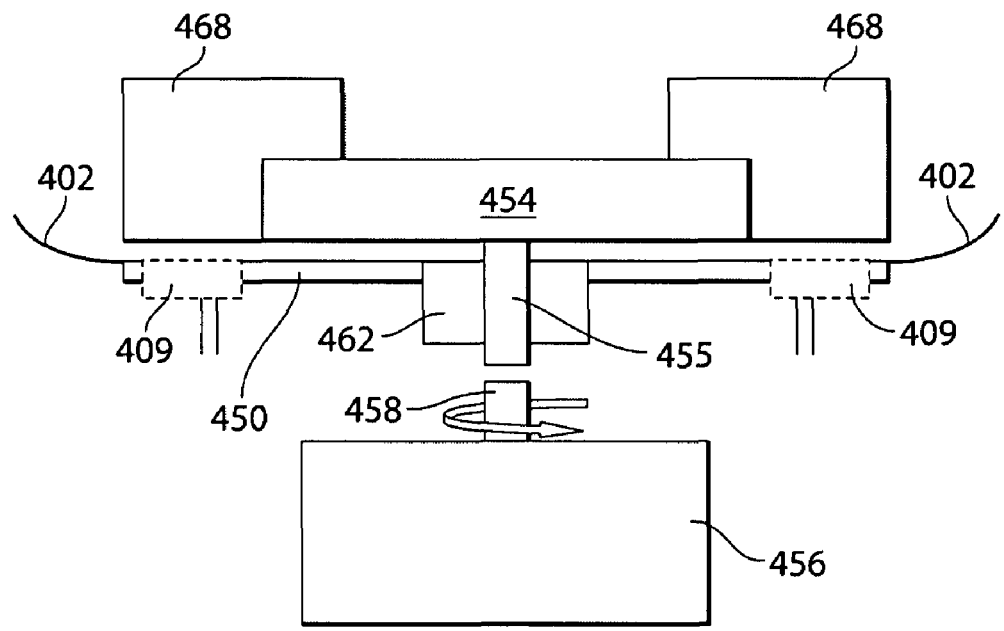

FIG. 10B illustrates another embodiment, having a mechanically-driven impeller. As shown, this embodiment generally includes an impeller support 450, an impeller hub 454 with shaft 455, and an external motor 456 with shaft 458. The connection of shafts between the impeller hub shaft and the motor shaft may be accomplished in a matter familiar to one of ordinary skill in the art (e.g., gear box, hex drive, or the like).

The impeller support can be affixed, for instance, to a side of the bioreactor wall 402 at a lower portion thereof. The impeller support may be affixed to the wall of a container by any of the methods described herein. Porous, micro-porous, or ultrafiltration elements 409 may also be included in the present embodiment to allow gaseous sparge or fluids into and out of the bioreactor, as discussed in detail below. In the embodiment illustrated in FIG. 10B, the shaft of the impeller hub may be received in a seal 462 (which may also include a bearing, in some cases) centrally located in an impeller support 450. The seal can be used to prevent or reduce contamination of the contents of the container. The impeller hub can also be maintained at a slight distance above the surface of the impeller support to prevent friction therebetween. The impeller hub may include one or more impeller blades 468, or other suitable mixing structures, such as vanes, plates, cones, etc. Careful and close alignment, vertically and horizontally, between the drive head and impeller support can add significant benefits to mixing devices described herein.

Figure 11:
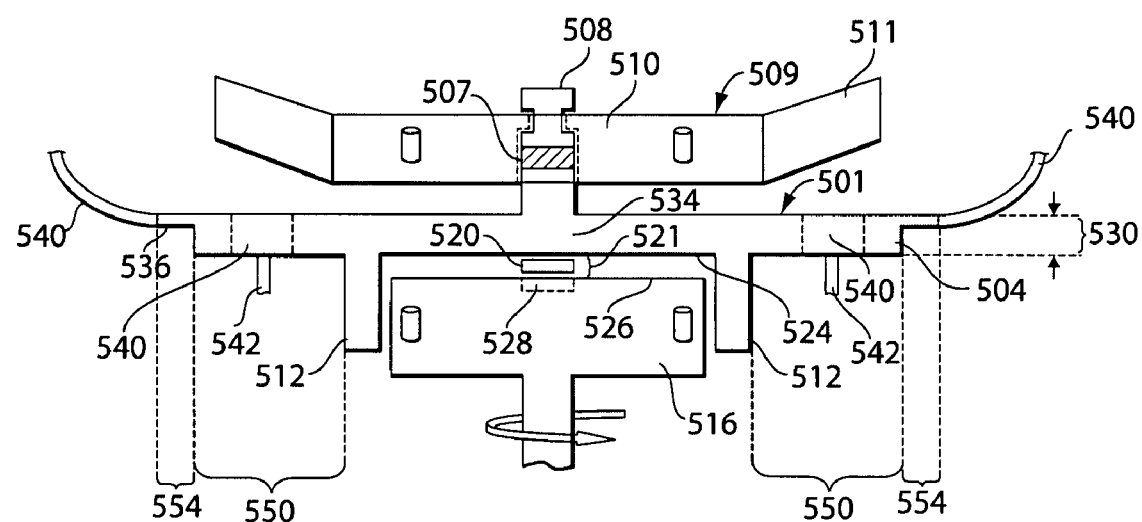
FIG. 11 shows an impeller magnetically coupled to an external motor, according to another embodiment of the invention.

Referring now to FIG. 11, one embodiment of a drive head magnetically coupled to an impeller is illustrated schematically. In FIG. 11, a system 500 including an impeller support 501, shown in a cross-section, includes a substantially horizontal portion 504, from which a substantially vertical impeller shaft 508 extends upwardly supporting an impeller 509 (which may include a core 510 and blades 511). Impeller 509 may rotate about shaft 508. Optionally, this rotation may be facilitated by a bearing 507, which may be any suitable bearing such as a roller bearing, ball bearing (e.g., a radial axis ball bearing), thrust bearing, race bearing, double raceway bearing, lazy-susan bearing, or the like. Impeller support 501 includes drive head alignment elements 512 which, in the embodiment illustrated, are substantially vertical downwardly-depending ridges which can define a circular recess into which at least a portion of a drive head 516 can be inserted. Guide elements 512 are positioned such that drive head, when engaged with the impeller support, position the drive head at a predetermined desired location relative to impeller 509. In one arrangement, guide elements 512 center the drive head, when engaged with the impeller support, with respect to impeller 509. As a further, optional embodiment, a physical spacer 520 can be provided between drive head 516 and a bottom surface 524 of the impeller support aligned with that portion of the top surface 526 of the drive head at the location at which the drive head is ideally positioned with respect to the impeller support. Physical spacer 520 physically separates, by a desired distance, bottom surface 524 of the impeller support with a top surface 526 of the drive head, but, at least one portion between top surface 526 and bottom surface 524 may define a continuous, physical connection (free of voids of air or the like) between the drive head and the impeller support. This allows for closer tolerance of the drive head with the impeller support than would have been realized in many prior arrangements, and it allows for reproducible and secure engagement of the drive head with the impeller support. In some cases, the drive head includes a recess 528 into which at least a portion of physical spacer 520 can be inserted. This arrangement can allow reproducible and secure engagement of the drive head with the physical spacer.

The bottom of the impeller support and the top surface of the drive head can be separated (e.g., using a physical spacer) by a distance 521. In one embodiment, distance 521 is no greater than 50% of average thickness 530 of the substantially horizontal portion 504 of the impeller support. In other embodiments, this distance is no more than 40%, 30%, 20%, 10%, or 5% of the thickness of the impeller support.

In some embodiments, physical spacer 520 has a thickness no greater than 50% of average thickness 530 of the substantially horizontal portion 504 of the impeller support. In other embodiments, this thickness is no more than 40%, 30%, 20%, 10%, or 5% of the thickness of the impeller support.

In one set of embodiments, physical spacer 520 is a bearing that facilitates rotation of the drive head relative to the impeller support. Where physical spacer 520 is a bearing, any suitable bearing can be selected such as a roller bearing, ball bearing (e.g., a radial axis ball bearing), thrust bearing, race bearing, double raceway bearing, lazy-susan bearing, or the like.

In the embodiment illustrated in FIG. 11, the drive head can vary in position, relative to shaft 508, horizontally no more than 5 mm during normal operation or, in other embodiments, no more than 4, 3, 2, 1 (0.5, or 0.25 mm during normal operation). The drive head can also vary in distance relative to bottom surface 524 of the impeller support by no more than 10 mm, 1 mm, 0.5 mm, 0.25 mm, 0.1 mm, or 0.005 mm in certain embodiments with the use of the arrangements illustrated in FIG. 11.

The arrangements of FIG. 11, especially in embodiments where physical spacer 520 is used, also adds physical support to impeller support 501 in addition to any other physical support which the impeller support 501 might receive. This added support is particularly advantageous in collapsible bag arrangements including impellers (e.g., for mixers and/or antifoaming devices).

Optionally, impeller support 501 may include spargers 540 positioned beneath blades of the impeller. The spargers can be dimensioned for connection to one or more sources of gas. For example, the spargers may include a port that can be connected to tubing 542 in fluid communication with one or more sources of gas.

Although figures illustrated herein may show impellers that are positioned at or near a bottom portion of a container, in other embodiments, impellers can be positioned at any suitable location within a container, for example, near the center or a top portion of a container. This can be achieved by extending the length of a shaft which supports the impeller, or by any other suitable configuration. Positions of impellers in a container may depend on the process to be performed in the container. For instance, in some embodiments where sparging is required, impellers may be positioned near the sparger such that the impeller can sweep and/or regulate the bubbles introduced into the container. Additionally, although the figures described herein show a single impeller associated with a shaft, more than one impeller can be used in some instances. For example, a first impeller coupled to a shaft may be located near a bottom portion of the container and a second impeller coupled to the shaft may be positioned near the center of the container. The first impeller may provide adequate sweeping of a sparged gas, and the second impeller may provide adequate mixing of contents within the container.

In some embodiments, the impeller support is uniquely designed to be readily fastenable to a collapsible bag. Certain known arrangements of impellers attached to collapsible bags may suffer from drawbacks resulting from non-ideal attachment of the bag to the impeller support, or non-ideal techniques for such attachment, or both. As shown in the embodiment illustrated in FIG. 11, an impeller support may include a base, substantially perpendicular to a shaft upon which the impeller rotates, having a first portion 534 of a certain average thickness, and a second, peripheral portion 536 thinner and optionally more flexible than the first portion for facilitating attachment to the bag. The first portion thickness is defined as the overall thickness cross-section taken up by the first portion at any point and, where the first portion includes a ribbed or other structure including various thicknesses, the thickness for purposes of this discussion is defined as the thickest portion. The second, peripheral portion, in one embodiment, defines a composition similar to or essentially identical to that of the collapsible bag, and is provided in a thickness similar to that of the collapsible bag. In other embodiments, the second, peripheral portion is formed by a composition different than that of the collapsible bag. For instance, in some embodiments, the first portion is formed in low density polyethylene, and the second portion is formed in high density polyethylene, polypropylene, silicone, polycarbonate, and/or polymethacrylate.

A vessel to which mixing system 500 is associated may support portions of the system such that the system does not break, bend, and/or collapse under the weight of the contents in the vessel. As such, first portion 534 and/or second portion 536 may have suitable average thicknesses and may be formed in suitable materials such that one or both portions are sufficient to adequately support the impeller shaft and/or the support structure itself during use, or under the weight of any contents contained in the vessel. Depending on the size and design of the vessel, in some embodiments, the support structure (e.g., vessel 114 which may be in the form of a reusable support structure) extends under area 554 (e.g., the second portion) to support area 554, leaving area 550 unsupported and exposed to atmosphere 20 outside of the vessel. In such embodiments, second portion 536 may be rigid and/or may be formed in a sufficiently strong material. In other embodiments, the vessel extends under both areas 554 and 550. In some cases, the system may be designed so that much of the strength of the system arises from area 550 of first portion 534. Accordingly, first portion 534 may be rigid and/or may be formed in a sufficiently strong material, while second portion 536 may be flexible and/or unable to support itself under the weight of contents contained in the vessel. In other cases, both the first and second portions can support themselves under the weight of contents contained in the vessel.

The thickness of the peripheral portion of the impeller support and the thickness of the walls of collapsible bag 540, prior to attachment, may differ by no more than 100%, or by no more than 80%, 60%, 40%, 20%, or 10% in other embodiments (e.g., as a percentage of the greater thickness between the walls of the bag and the peripheral portion). Where the thickness of the peripheral portion of the impeller support and the thickness of the disposable bag (at least the portion attachable to the impeller support) are made of similar (or compatible) materials and are of similar thickness, then joining of one to the other can be facilitated easily, reproducibly, and with a product that is free of significant irregularity and thickness in the transition of the bag to the impeller support attachment portion. As described herein, joining of the bag and the support can be performed by any suitable method including, for example, molding and welding (e.g., ultrasonic or heat welding).

Figure 12:
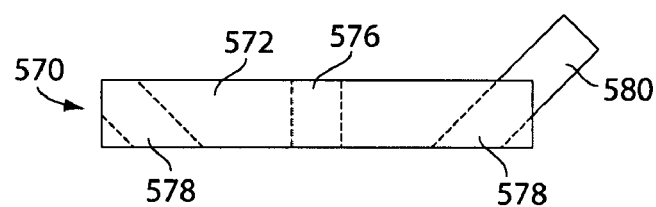
FIG. 12 shows an impeller, according to an embodiment of the invention.

In some embodiments, impellers with replaceable blades can be used with apparatuses described herein. FIG. 12 illustrates an impeller 570 that includes a hub 572, which can have a generally circular outer perimeter and may include a center passage 576 before within which the impeller shaft or post (not illustrated) resides. Hub 572 includes one or more slots 578 within which one or more impeller blades 580 can, in some embodiments, be replaceably inserted. As illustrated, one slot 578 is shown not containing a blade and one slot 578 is shown containing an impeller blade. The blade and blade slots are illustrated very schematically and, of course, those of ordinary skill in the art will recognize that a variety of different sizes, shapes, and pitches of blades and slots can be selected by those of ordinary skill in the art for a variety of mixing purposes described herein and known in the art. Blades 580 can be positioned and held within slots 578 securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives.

The replaceable blade arrangement of the invention as illustrated in FIG. 12 provides the advantage in that different blades can be used with a single hub in a mixing/rotating arrangement so that the arrangement can be used for different purposes or involving different rotational speed, torque, mixing profile, or the like. For example, blades of a first size or pitch can be replaced with blades of a second size or pitch to create greater or lesser sheer, aeration, mixing or the like as would be understood by those of ordinary skill in the art. While replaceable blades (e.g., airplane propeller blades) are known in different fields, replaceable blades in a collapsible bag arrangement such as that described herein would not have been expected to have been found based upon knowledge in the art because such bags typically were used only for mixing media containing cells which, to avoid being lysed, must be stirred below a threshold of sheer, or for media containing other materials which can tolerate much higher sheer. However, as described herein, collapsible bag arrangements can be prepared with multiple blades and provided for use with either or both of two or more mixing profiles.

In some cases, the impeller (in some embodiments, via magnetic coupling of the drive head to the impeller) is driven by a motor able to reverse its direction of rotation and/or to be finely tuned with respect to rotational speed. Reversal of direction of spin provides significant advantage in producing a variety of aeration/sparger profiles, or the like. Furthermore, fine tuning of impeller speed can allow for a precise and controllable degree and/or balance of aeration/sparging, sheer, or the like, which has been determined to be quite useful in connection with various media for mixture, especially those including cells. Such embodiments allow for reproducible and controllable adjustment of rotational speed of the impeller that amounts of plus or minus 5% or less through a range of rotational speeds of between 10% and 90% of total maximum impeller rotational speed. In other embodiments, rotational tuning of 4%, 3%, 2%, or 1% of this speed is facilitated. In one arrangement, these aspects are realized by use of a servo motor.

In certain embodiments, multiple spargers (including sparging elements) that may be dimensioned for connection to different sources of gas and/or which may be independently controlled are associated with apparatuses described herein. The type of gas, number of spargers, and types and configurations of spargers used in an apparatus (e.g., a bioreactor system or a biochemical/chemical reaction system) may depend, in part, on the particular process to be carried out (e.g., an aerobic versus anaerobic reaction), the removal of any toxic byproducts from the liquid, the control of pH of a reaction, etc. As described in more detail below in connection with certain embodiments described herein, a system may include separate spargers for different gases which may have different functions in carrying out, for example, a chemical, biochemical and/or biological reaction. For instance, a bioreactor system for cell cultivation may include different types of gases such as a "dissolved oxygen (DO) control gas" for controlling the amount of dissolved oxygen in the culture fluid, a "strip gas" for controlling the amount of toxic byproducts in the culture fluid, and a "pH control gas" for controlling the pH of the culture fluid. Each type of gas may be introduced into the culture using different spargers that can be independently operated and controlled. Advantageously, such a system may provide faster process control and less process control variability (compared to, for example, certain systems that combine a DO control gas, strip gas, and pH control gas into one gas stream introduced into a reactor). Chemical, biochemical and/or biological reactions carried out in bioreactor systems described herein may also require lower consumption of gas which can save money on expensive gases, and/or less total gas flow rate (e.g., for a strip gas), which can reduce foam generation and/or reduce the size of inlet gas sterile filters required.

In some embodiments, vessels described herein are a part of a bioreactor system. In bioreactors used for certain types of cell cultivation, cells may require nutrients such as sugars, a nitrogen source (such as ammonia ($NH_3$) or amino acids), various salts, trace metals and oxygen to grow and divide. Like the other nutrients, even and uniform distribution of oxygen throughout the reactor may be essential to provide uniform cell growth. Poor distribution of oxygen can create pockets of cells deprived of oxygen, leading to slower growth, alteration of the cell metabolism or even cell death. In certain applications where the cells are engineered to produce a bioproduct, oxygen deprivation can have a sever affect on the quantity and quality of bioproduct formation. The amount of nutrients available to cells at any one time depends in part on the nutrient concentration in the fluid. Sugars, nitrogen sources, salts, and trace metals may be soluble in fluid and, therefore, may be in excess and readily available to the cells. Oxygen, on the other hand, may be relatively poorly soluble or "dissolved" in water. In addition, the presence of salts plus the elevated temperature necessary to grow cells may further reduce dissolved oxygen concentration. To compensate, a rapid dissolved oxygen sensing system, constant and steady transfer of oxygen into the fluid (e.g., using one or more spargers as described herein), combined with rapid and even distribution in the bioreactor may be used to reduce or prevent oxygen starvation.

Since oxygen transfer from the gas bubbles entering the fluid of the culture may be an important control parameter, the time constant of responsiveness of the gas delivery system may also be important. In certain embodiments, as cell population density increases, the response rate of the gassing system to supply oxygen:enriched DO control gas may become increasingly important. Accordingly, in some embodiments, systems described herein include one or more sensors such as a DO sensor which detects the need for more oxygen (or other gas), a gas controller, and one or more spargers which can be signaled to enrich the culture with extra oxygen using, for example, a $N_2/O_2$/air control gas. Since delay time (e.g., several minutes) for this enriched gas to reach the reactor can result in a drop in DO which can lead to oxygen starvation, systems described herein may include a control feedback loop between the sensor(s), gas controller, and sparger(s). Thus, responsive, and even supply and distribution of oxygen-bearing control gas (e.g., a $N_2/O_2$/air mix) may be provided for controlled, predictable cell growth and bioproduct formation. Systems described herein allowing independent control of spargers and/or gas compositions may be advantageous compared to systems that require gases to be flushed out before sparging a different gas into the container.

In addition, since compressed air and oxygen may be expensive to supply to the reactor, a system that provides just enough air enriched with just enough oxygen such that the bubbles are not lost to the head space of the container (and lost out through the exhaust line) may be implemented. This can be performed, for example, by controlling the amount and flow rate of a control gas independently of other gases used in the system (e.g., a strip gas and/or a pH control gas).

Without wishing to be bound by any theory, it is believed that the rate of oxygen transfer into the bioreactor fluid from air, pure oxygen or a gas mixture is directly related to the amount of total surface area of the bubbles in the fluid. Hence, larger bubbles provide less total surface area than a fine mist of very small bubbles. For this reason, in certain embodiments of the invention, a control gas may be provided through microporous spargers to create very small bubbles. A microporous sparger may include apertures having a size (e.g., average diameter) of, for example, less than less than 500 microns, less than 200 microns, less than 100 microns, less than 60 microns, less than 50 microns, less than 40 microns, less than 30 microns, less than 20 microns, less than 10 microns, less than 3 microns, less than about 1 micron, or less than 0.1 microns. In certain embodiments, microporous spargers have an aperture size between 0.1 and 100 microns. Of course, spargers having larger aperture sizes may also be used. For instance, a sparger may have an aperture size between 0.1 and 10 mm. The aperture size may be greater than 100 microns, greater than 200 microns, greater than 500 microns, greater than 1 mm, greater than 3 mm, greater than 5 mm, greater than 7 mm, or greater than 10 mm. The aperture may have any suitable cross-sectional shape (e.g., circular, oval, triangular, irregular, square or rectangular, or the like). Spargers having combinations of aperture sizes can be incorporated into vessels described herein.

Additionally, good cell growth and controlled metabolism may be dependent upon removal of toxic byproducts of cell growth, such as, for example, carbon dioxide, ammonia and volatile organic acids. Carbon dioxide may be highly soluble in water, which can exacerbate its toxic effect on cells. These byproducts can be "stripped" out of the culture fluid by gassing the culture using a strip gas. Accordingly, even distribution of strip gas and strip gas that is introduced at a flow rate sufficiently high enough for bubbles to escape out of the culture (and out the exhaust vent, for example) may be important for cell growth and/or bioproduct production. These parameters may be controlled independently of other gases used in the system (e.g., a control gas and/or a pH control gas) using a separate sparger for the strip gas.

In some instances, a strip gas is introduced into a container using a sparger having an aperture size between 0.1 and 10 mm. For example, the aperture size may be greater than 100 microns, greater than 200 microns, greater than 500 microns, greater than 1 mm, greater than 3 mm, greater than 5 mm, greater than 7 mm, or greater than 10 mm. These aperture sizes can allow relatively larger bubbles to pass through the liquid of the container, which can strip any toxic byproducts out of the liquid without creating large amounts of foam in the head space of the container.

In certain embodiments, a pH control gas is used to control the pH of the fluid in a bioreactor system. For example, carbon dioxide may be used to increase solution pH and ammonia may be used to decrease solution pH. In one embodiment, a pH control gas may include a combination of carbon dioxide, ammonia, or other gases to control (e.g., increase or decrease) pH. In another embodiment, the pH of a reaction fluid is controlled by a first sparger containing an agent that increases pH (e.g., $CO_2$) and a second sparger containing an agent that decreases pH (e.g., $NH_3$).

One or more pH control gases may be added to a container of the bioreactor system upon signals from a pH control sensor associated with the system. The pH control gases may be operated independently and without interference by oxygen demand (e.g., a DO control gas) or strip gas systems. A pH control gas may be introduced into a container using spargers having apertures of various sizes.

In other embodiments, cells that are normally grown without oxygen (e.g., anaerobic reactions) or which are even sensitive to oxygen require removal of oxygen from the culture. Even and controlled distribution of nitrogen gas in these cultures may be used to control proper cell growth and product formation.

As mentioned, in some embodiments of the present invention, gases such as air, $CO_2$, $O_2$, $N_2$, $NH_3$, and/or dissolved oxygen may be sparged into the container. In some cases, the sparging can be controlled, for instance, such that the sparging can be rapidly activated or altered as needed. Multiple spargers may be used in some cases. For example, in one embodiment, different gas compositions may each be introduced into the container using multiple spargers, e.g., a first sparger for a first gas composition, a second sparger for a second gas composition, a third sparger for a third gas composition, etc. The gases may differ in composition and/or in concentration. As a specific example, a first gas composition may include air with 5% $CO_2$, and a second gas composition may include air with 10% $CO_2$; in another example, a first gas composition may include $O_2$, and a second gas composition may include $N_2$; in yet another example, a first gas composition may include a control gas, a second gas composition may include a strip gas, and a third gas composition may include a pH control gas. Of course, other combinations of gases are also possible. In some cases, multiple spargers may be useful to allow faster responses, e.g., as the gas composition being introduced into the container may be rapidly changed by activating different spargers, e.g., singly and/or in combination. As a specific example, the gas being introduced into a container can be rapidly switched from a first gas (via a first sparger) to a second gas (via a second sparger), and/or to a combination of the first and second gas, or a combination of the second gas and a third gas, etc. The flow rates of each gas can also be changed independently of one another. (In contrast, with a single sparger, a change in composition requires that the new composition reach the sparger before being introduced into the container.) Moreover, the use of multiple spargers can allow customization of the type of sparger for a particular type of gas, e.g., a strip gas, DO control gas, pH control gas, air, $CO_2$, $O_2$, $N_2$, $NH_3$, or any other suitable gas, if desired.

Sparging may be run continuously, periodically, or in some cases, in response to certain events, e.g., within a bioreactor system and/or within the container. For example, as mentioned, the spargers may be connected to one or more sensors and a control system which is able to monitor the amount of sparging, the degree of foaming, the amount or concentration of a substance in the container, and respond by initiating, reducing, or increasing the degree of sparging of one or more composition(s) of gases.

In one particular embodiment, a vessel (e.g., as part of a reactor system for performing a biological, biochemical or chemical reaction) is configured to contain a volume of liquid and includes a container (e.g., a collapsible bag) having a volume of at least 2 liters (or any other suitable volume) to contain the volume of the liquid. The vessel may optionally include a support structure for surrounding and containing the container. Additionally, the vessel includes a first sparger connected or dimensioned to be connected to a source of a first gas composition in fluid communication with the container, and a second sparger connected or dimensioned to be connected to a source of a second gas composition different from the first gas composition in fluid communication with the container. The vessel further comprises a control system operatively associated with the first and second spargers and configured to operate the spargers independently of each other. Of course, third, fourth, fifth, or greater numbers of spargers can be included (e.g., greater than 10, or greater than 20 spargers), depending on, for example, the size of the container. In some embodiments, the vessel further comprises a mixing system including an impeller and a base plate, wherein the first and/or second spargers is associated with the base plate. The vessel may be part of an apparatus comprising at least one environmental containment enclosure at least partially surrounding and, optionally, attached to the vessel. In one particular embodiment, the first gas composition comprises air and the second gas composition comprises air supplemented with $O_2$ and $N_2$. If additional spargers are included, the spargers can be connected to a source of gas comprising $N_2$, $CO_2$, $NH_3$ and/or any other suitable gas.

In another exemplary embodiment, a vessel configured to contain a volume of liquid comprises a container (e.g., a collapsible bag) to contain the liquid, and optionally, a support structure for surrounding and containing the collapsible bag. The vessel includes a first sparger connected to the container, the first sparger having a first aperture size, wherein at least a portion of the first sparger is dimensioned to be connected to a source of a first gas composition. The vessel also includes a second sparger connected to the container, the second sparger having a second aperture size, wherein at least a portion of the second sparger is dimensioned to be connected to a source of a second gas composition. The second gas composition may have the same or a different composition than the first gas composition. In some embodiments, the vessel is part of a bioreactor system; or, the vessel may be a part of a biochemical/chemical reaction system, or a mixing system. The vessel may include a control system operatively associated with the first and second spargers and may be configured to operate the spargers (or gases associated therewith) independently of each other. The vessel may include any suitable number of spargers (e.g., greater than 10 or greater than 20 spargers), and the container may have any suitable volume (e.g., at least 2, 10, 20, 40, or 100 liters). The first and/or second gas composition(s) may include, for example, $N_2$, $O_2$, $CO_2$, $NH_3$, or air. For example, in one instance, the first gas comprises air and the second gas comprises air supplemented with $O_2$ and $N_2$. The first aperture size may be larger than the second aperture size. For instance, the first aperture size may be between 0.1 and 10 mm, and the second aperture size may be between 0.1 and 100 microns.

Apertures associated with spargers can be formed in any suitable material. For instance, in one embodiment, a porous polymeric material is used as a sparging element to allow transport of gas from one side to another side of the material. Apertures can also be formed in other materials such as metals, ceramics, polymers, and/or combinations thereof. Materials having pores or apertures can have any suitable configuration. For example, the materials may be knitted, woven, or used to form meshes or other porous elements. The elements may be in the form of sheets, films, and blocks, for example, and may have any suitable dimension. In some cases, such elements are incorporated with impellers or impeller supports, e.g., as illustrated in FIG. 11. The elements can be positioned and held within regions of the impeller or impeller support securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives. In other embodiments, portions of the impeller and/or impeller support can be fabricated directly with pores or apertures that can allow fluids to flow therethrough.

The vessel may optionally include one or more sensors in electrical communication with the control system for determining an amount or concentration of a gas (e.g., $O_2$, $N_2$, $CO_2$, $NH_3$, a bi-product of a reaction) in the container. Additionally and/or alternatively, the vessel may include a sensor in electrical communication with the control system for determining a pH of a liquid in the container, or an amount or level of a foam in the container (e.g., bag).

Figure 13:
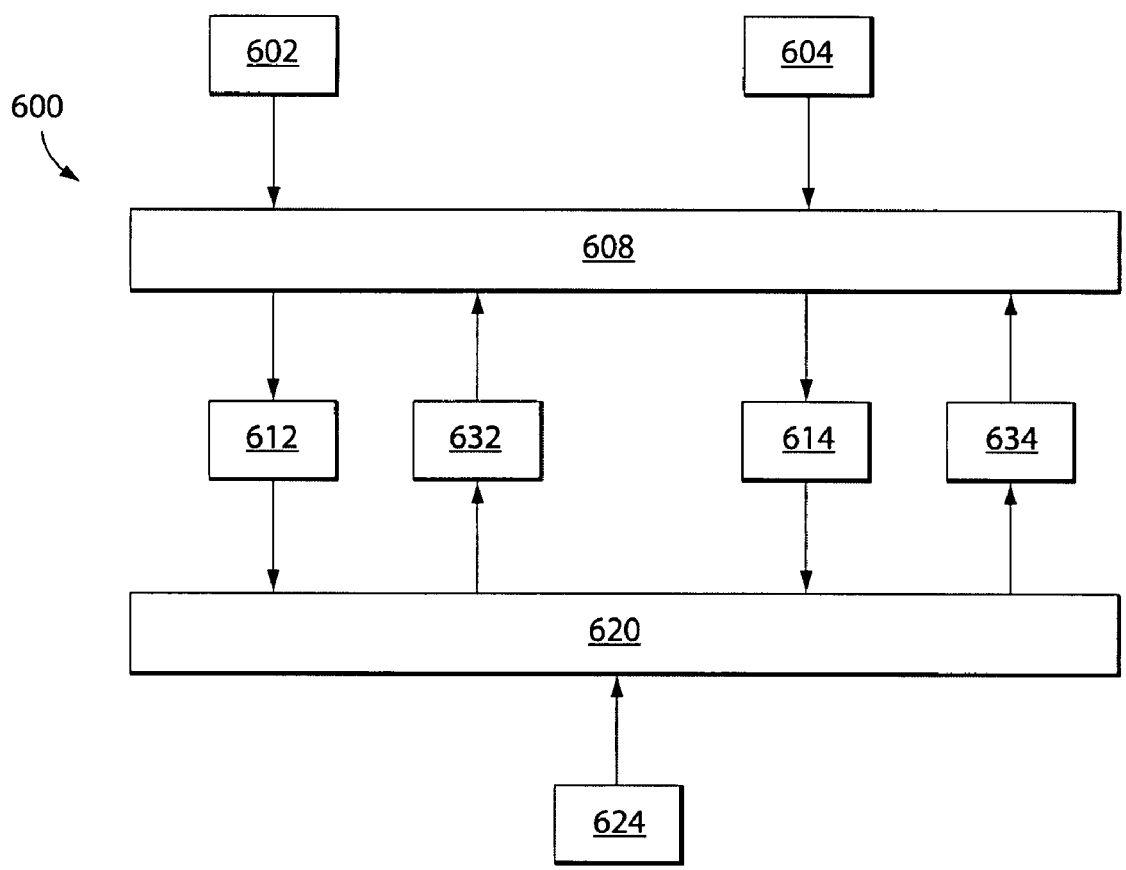
FIG. 13 shows an example of a control and feedback process for operating certain embodiments of the disclosed apparatuses and systems, according to an embodiment of the invention.

As mentioned, control systems and feedback loops may be used to control a variety of processes described herein, including the degree of sparging in one embodiment, or degree of mixing, or activity of a ventilation system in other embodiments. One example of such a control and feedback process is shown in the embodiment illustrated in FIG. 13. System 600 may include a first sensor 602 (e.g., for detecting the amount and/or concentration of $CO_2$ of a liquid in the container) and a second sensor 604 (e.g., for detecting the amount and/or concentration of $O_2$ of a liquid in the container). After calibrating the sensors, reagents may be added to a container 608 and a fluidic manipulation process, such as mixing or performing a biological, chemical, or biochemical reaction, may be take place. The amount of a gas such as $O_2$ and $CO_2$ may vary in the liquid of the container as the process proceeds. For example, if a biological reaction involving cells takes place, the cells may consume $O_2$ and form $CO_2$ over time, which may vary depending on the growth stage of the cells. Thus, the amount and/or concentration of gases can be determined by the sensors (e.g., as a function of time), and signals 612 and 614 related to the amounts and/or concentrations of the gases can be sent to a control system 620. The control system may include recorded parameters 624, such as threshold levels of one or more gases that can inputted by a user prior to or during the reaction. For example, a parameter may include a certain threshold level of $CO_2$ in the liquid before a sparger is activated to reduce the amount of $CO_2$ using a strip gas. Accordingly, a signal may be sent from the control system to activate a component 632, such as a valve connected to a source of a strip gas used to reduce the amount of $CO_2$. As the strip gas is introduced into container 608, the amount and/or concentration of $CO_2$ may decrease, which can be measured by 612 and signals sent to the control system. When the amount and/or concentration of $CO_2$ decreases to a certain level, the control system can lower or deactivate the amount of $CO_2$ being introduced into the container, thereby completing the feedback loop. A similar process can take place independently of the process described above using second sensor 614, which may measure, for example, a second gas, a pH, or an amount of a foam in a head space of the container. In other embodiments, a similar process may be performed for measuring the amount of particulate material in an environmental containment enclosure and activation/regulation of an environmental treatment process.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified.

Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus comprising:
   a vessel or a processing device having an interior comprising a container adapted for containing a liquid;
   an environmental containment enclosure having an inner surface and configured for surrounding at least a portion of the vessel or the processing device, the environmental containment enclosure being configured so that at least a portion of the environmental containment enclosure has a shape and/or contour that is complementary to a shape and/or contour of an outer surface of the vessel or an outer surface of the processing device to which the at least a portion of the environmental containment enclosure is adjacent;
   the inner surface of the environmental containment enclosure and the outer surface of the vessel or the processing device defining an enclosed space therebetween, at least a portion of said enclosed space not in continuous fluid communication with an interior portion of the container, and wherein said enclosed space is maintained during use of the vessel or the processing device at a pressure chosen from greater than atmospheric pressure, less than atmospheric pressure, and equal to atmospheric pressure;
   an environmental treatment system in communication with the enclosed space, the environmental treatment system comprising a ventilation system in fluid communication with the enclosed space, the ventilation system comprising an inlet port dimensioned for connection to a source of gas unit for introducing gas into the apparatus and an outlet port for connection to an exhaust unit for removing a gas from the apparatus; and
   a damper control configured for connection to at least one of the source of gas unit and the exhaust unit, the damper control capable of regulating pressurization within the apparatus; and
   wherein the environmental treatment system and environmental containment enclosure are configured to maintain an aseptic and/or substantially particle-free environment within the enclosed space.

2. An apparatus as in claim 1, wherein the interior of the vessel or the processing deive is operated at a pressure greater than atmospheric pressure.

3. An apparatus as in claim 2, wherein the ventilation system comprises a particulate measurement system.

4. An apparatus as in claim 1, wherein the vessel defines a rigid container adapted for containing a liquid, wherein inner walls of the vessel are in direct contact with the liquid.

5. An apparatus as in claim 1, wherein the vessel comprises a collapsible bag adapted for containing a liquid and defines a support structure adapted for surrounding and supporting the collapsible bag.

6. An apparatus as in claim 1, wherein the environmental containment enclosure comprises at least one access port selected independently from the group consisting of an iris port, a glove port, a septum, and a valve, said access port arranged to allow access to a liquid in the container or to the processing device without the liquid or the processing device being subjected to an atmosphere surrounding the environmental containment enclosure.

7. An apparatus as in claim 1, wherein only a portion, but not all, of the vessel is enclosed by the environmental containment enclosure.

8. The apparatus of claim 1, wherein the enclosed space is maintained at a pressure greater than atmospheric pressure during use of the vessel.

9. The apparatus of claim 2, wherein the enclosed space is maintained at a pressure less than atmospheric pressure during use of the vessel.

10. An apparatus comprising:
   at least one device comprising a vessel or a processing device having an outer surface and an interior portion configured for containing a fluid or biological cells;
   a first environmental containment enclosure having an inner surface and configured for surrounding at least a portion of the vessel or the processing device,
   the inner surface of the environmental containment enclosure and the outer surface of the vessel or the processing device defining a first enclosed space therebetween, said first enclosed space not in continuous fluid communication with the interior portion of the vessel or the processing device;
   a second environmental containment enclosure surrounding at least a portion of the first environmental containment enclosure, the second environmental containment enclosure having an inner surface, the inner surface of the second environmental containment enclosure and the outer surface of the first environmental containment enclosure defining a second enclosed space therebetween,
   said second enclosed space not in continuous fluid communication with the interior portion of the vessel or the processing device, and wherein said first and said second enclosed spaces are each maintained during use of the vessel or the processing device at a pressure chosen independently from greater than atmospheric pressure, less than atmospheric pressure, and equal to atmospheric pressure;
   an environmental treatment system in communication with at least one of the first and second enclosed spaces, the environmental treatment system comprising a ventilation system in fluid communication with at least one of the first and second enclosed spaces the ventilation system comprising an inlet port dimensioned for connection to a source of gas unit for introducing gas into the apparatus and an outlet port for connection to an exhaust unit for removing a gas from the apparatus; and
   a damper control configured for connection to at least one of the source of gas unit and the exhaust unit, the damper control operably connected to the apparatus and capable of regulating pressurization within the first and the second enclosed space of the apparatus; and wherein the environmental treatment system and the first and second environmental containment enclosures are configured to maintain an aseptic and/or substantially particle-free environment within the at least one of the first and second enclosed spaces.

11. An apparatus as in claim 10, comprising a third, substantially closed environmental containment enclosure configured to contain the first and the second environmental containment enclosures and to contain a leakage of any materials from an inner system.

12. An apparatus as in claim 10, wherein the interior portion of the vessel or the processing device is maintained at a pressure greater than atmospheric pressure during use of the vessel.

13. An apparatus as in claim 10, wherein at least one of the first enclosed space, the second enclosed space, and the vessel is maintained at a pressure less than atmospheric pressure during use of the vessel.

14. An apparatus as in claim 10, wherein the vessel comprises a collapsible bag adapted for containing a liquid and includes a support structure adapted for surrounding and supporting the collapsible bag.

15. An apparatus as in claim 10, wherein the vessel or the processing device is in the form of a unit operation component adapted for performing a biological, chemical, and/or pharmaceutical manufacturing process.

16. The apparatus of claim 10, wherein at least one of the first and the second environmental containment enclosures comprises at least one access port selected independently from the group consisting of an iris port, a glove port, a septum, and a valve, said access port arranged to allow access to the interior portion of the vessel or the processing device without the interior portion of the vessel or the processing device being subjected to an atmosphere surrounding the second environmental containment enclosure.

17. The apparatus of claim 10, wherein the ventilation system is in fluid communication with the first enclosed space, the apparatus having a configuration wherein the interior portion of the vessel or the processing device is at a first pressure greater than atmospheric pressure; the first enclosed space is at a second pressure less than the first pressure; and the second enclosed space is at a third pressure greater than the second pressure in the first enclosed space; the configuration thereby allowing a material that enters the first enclosed space from the second enclosed space to be removed by the ventilation system.

* * * * *